United States Patent
Nagourney et al.

(10) Patent No.: US 11,181,524 B2
(45) Date of Patent: Nov. 23, 2021

(54) METABOLOMIC SIGNATURES FOR PREDICTING, DIAGNOSING, AND PROGNOSING VARIOUS DISEASES INCLUDING CANCER

(71) Applicant: Metabolomycs, Inc., Long Beach, CA (US)

(72) Inventors: Robert Nagourney, Long Beach, CA (US); Ismael Silva, Sau Paulo (BR); Paulo D'Amora, San Paulo (BR)

(73) Assignee: Metabolomycs, Inc, Long Beach, CA (US)

( * ) Notice: Subject to any disclaimer, the term of this patent is extended or adjusted under 35 U.S.C. 154(b) by 0 days.

(21) Appl. No.: 16/442,087

(22) Filed: Jun. 14, 2019

(65) Prior Publication Data

US 2019/0383819 A1 Dec. 19, 2019

Related U.S. Application Data

(60) Provisional application No. 62/685,275, filed on Jun. 14, 2018, provisional application No. 62/714,650, filed on Aug. 3, 2018, provisional application No. 62/830,389, filed on Apr. 6, 2019, provisional application No. 62/838,683, filed on Apr. 25, 2019.

(51) Int. Cl.
| | | |
|---|---|---|
| *G16H 50/30* | (2018.01) | |
| *G01N 33/574* | (2006.01) | |
| *G01N 33/68* | (2006.01) | |
| *G01N 33/92* | (2006.01) | |

(52) U.S. Cl.
CPC ..... *G01N 33/57449* (2013.01); *G01N 33/574* (2013.01); *G01N 33/6812* (2013.01); *G01N 33/6848* (2013.01); *G01N 33/92* (2013.01); *G01N 2800/067* (2013.01); *G01N 2800/50* (2013.01); *G01N 2800/52* (2013.01); *G01N 2800/60* (2013.01)

(58) Field of Classification Search
None
See application file for complete search history.

(56) References Cited

U.S. PATENT DOCUMENTS

| | | | |
|---|---|---|---|
| 2009/0176218 A1 | 7/2009 | Cheng et al. | |
| 2011/0033377 A1* | 2/2011 | Autelitano | ....... G01N 33/57449 424/1.11 |
| 2012/0197539 A1 | 8/2012 | Slupsky | |
| 2014/0297195 A1 | 10/2014 | Keller et al. | |
| 2016/0377623 A1 | 12/2016 | Ritchie et al. | |
| 2017/0156627 A1 | 6/2017 | Bahado-Singh et al. | |
| 2017/0299592 A1 | 10/2017 | Lopes Carvalho et al. | |

OTHER PUBLICATIONS

Anna Bachmayr-Heyda et al, Integrative Systemic and Local Metabolomics with Impact on Survival in High-Grade Serous Ovarian Cancer, Clinical Cancer Research, Oct. 19, 2016, 2081-2092, 23(8), online at https://clincancerres.aacrjournals.org/content/23/8/2081.

\* cited by examiner

*Primary Examiner* — Paul S Hyun
(74) *Attorney, Agent, or Firm* — Fitzsimmons IP Law

(57) ABSTRACT

A system and method for using new biomarkers to assess individual diseases is provided. In one embodiment of the present invention, absolute quantification of annotated metabolites by mass spectrometry is used to identify certain biomarkers and derivatives thereof (i.e., signatures), which are then used to screen for, diagnose, predict, prognose, and treat various diseases, including, but not limited to, breast cancer, ovarian cancer, colorectal cancer, pancreatic cancer, and acute graft-versus-host disease.

10 Claims, 21 Drawing Sheets

| Analyte | Analyte | Analyte | Analyte |
|---|---|---|---|
| Alanine (Ala) | Leucine (Leu) | Valine (Val) | Methioninesulfoxide (Met-SO) |
| Arginine (Arg) | Lysine (Lys) | Acetylornithine (Ac-Orn) | Nitrotyrosine (Nitro-Tyr) |
| Asparagine (Asn) | Methionine (Met) | Asymmetric dimethylarginine (ADMA) | Hydroxyproline (OH-Pro) |
| Aspartate (Asp) | Ornithine (Orn) | Symmetric dimethylarginine (SDMA) | Phenylethylamine (PEA) |
| Citrulline (Cit) | Phenylalanine (Phe) | Total dimethylarginine (Total DMA) | Putrescine |
| Glutamine (Gln) | Proline (Pro) | Alpha-Aminoadipic acid (Alpha-AAA) | Sarcosine |
| Glutamate (Glu) | Serine (Ser) | Carnosine | Serotonin |
| Glycine (Gly) | Threonine (Thr) | Creatinine | Spermidine |
| Histidine (His) | Tryptophan (Trp) | Histamine | Spermine |
| Isoleucine (Ile) | Tyrosine (Tyr) | Kynurenine | Taurine |

Figure 2

| Analyte |
|---|
| Hydroxysphingomyelin with acyl residue sum C14:1 (SM (OH) C14:1) |
| Hydroxysphingomyelin with acyl residue sum C16:1 (SM (OH) C16:1) |
| Hydroxysphingomyelin with acyl residue sum C22:1 (SM (OH) C22:1) |
| Hydroxysphingomyelin with acyl residue sum C22:2 (SM (OH) C22:2) |
| Hydroxysphingomyelin with acyl residue sum C24:1 (SM (OH) C24:1) |
| Sphingomyelin with acyl residue sum C16:0 (SM C16:0) |
| Sphingomyelin with acyl residue sum C16:1 (SM C16:1) |
| Sphingomyelin with acyl residue sum C18:0 (SM C18:0) |
| Sphingomyelin with acyl residue sum C18:1 (SM C18:1) |
| Sphingomyelin with acyl residue sum C20:2 (SM C20:2) |
| Sphingomyelin with acyl residue sum C22:3 (SM C22:3) |
| Sphingomyelin with acyl residue sum C24:0 (SM C24:0) |
| Sphingomyelin with acyl residue sum C24:1 (SM C24:1) |
| Sphingomyelin with acyl residue sum C26:0 (SM C26:0) |
| Sphingomyelin with acyl residue sum C26:1 (SM C26:1) |

Figure 4

| Analyte | Analyte | Analyte |
|---|---|---|
| Carnitine (C0) | Octanoylcarnitine (C8) | Hydroxyhexadecadienylcarnitine (C16:2-OH) |
| Acetylcarnitine (C2) | Nonaylcarnitine (C9) | Hydroxyhexadecanoylcarnitine (C16-OH) |
| Propionylcarnitine (C3) | Decanoylcarnitine (C10) | Octadecanoylcarnitine (C18) |
| Propenoylcarnitine (C3:1) | Decenoylcarnitine (C10:1) | Octadecenoylcarnitine (C18:1) |
| Hydroxypropionylcarnitine (C3-OH) | Decadienylcarnitine (C10:2) | Hydroxyoctadecenoylcarnitine (C18:1-OH) |
| Butyrylcarnitine (C4) | Dodecanoylcarnitine (C12) | Octadecadienylcarnitine (C18:2) |
| Butenylcarnitine (C4:1) | Dodecenoylcarnitine (C12:1) | Decenoylcarnitine (C10:1) |
| Hydroxybutyrylcarnitine (C4-OH (C3-DC)) | Dodecanedioylcarnitine (C12-DC) | Decadienylcarnitine (C10:2) |
| Valerylcarnitine (C5) | Tetradecanoylcarnitine (C14) | Dodecanoylcarnitine (C12) |
| Tiglylcarnitine (C5:1) | Tetradecenoylcarnitine (C14:1) | Dodecenoylcarnitine (C12:1) |
| Glutaconylcarnitine (C5:1-DC) | Hydroxytetradecenoylcarnitine (C14:1-OH) | Dodecanedioylcarnitine (C12-DC) |
| Glutarylcarnitine* (Hydroxyhexanoylcarnitine) (C5-DC (C6-OH)) | Tetradecadienylcarnitine (C14:2) | Tetradecanoylcarnitine (C14) |
| Methylglutarylcarnitine (C5-M-DC) | Hydroxytetradecadienylcarnitine (C14:2-OH) | Tetradecenoylcarnitine (C14:1) |
| Hydroxyvalerylcarnitine (Methylmalonylcarnitine) (C5-OH (C3-DC-M)) | Hexadecanoylcarnitine (C16) | Hydroxytetradecenoylcarnitine (C14:1-OH) |
| Hexanoylcarnitine (Fumarylcarnitine) (C6 (C4:1-DC)) | Hexadecenoylcarnitine (C16:1) | Tetradecadienylcarnitine (C14:2) |
| Hexenoylcarnitine (C6:1) | Hydroxyhexadecenoylcarnitine (C16:1-OH) | Hydroxytetradecadienylcarntine (C14:2-OH) |
| Pimelylcarnitine (C7-DC) | Hexadecadienylcarnitine (C16:2) | Hexadecanoylcarnitine (C16) |

Figure 3

| Analyte | Analyte |
|---|---|
| Lysophosphatidylcholine with acyl residue C14:0 (lysoPC a C14:0) | Phosphatidylcholine with diacyl residue sum C34:4 (PC aa C34:4) |
| Lysophosphatidylcholine with acyl residue C16:0 (lysoPC a C16:0) | Phosphatidylcholine with diacyl residue sum C36:0 (PC aa C36:0) |
| Lysophosphatidylcholine with acyl residue C16:1 (lysoPC a C16:1) | Phosphatidylcholine with diacyl residue sum C36:1 (PC aa C36:1) |
| Lysophosphatidylcholine with acyl residue C17:0 (lysoPC a C17:0) | Phosphatidylcholine with diacyl residue sum C36:2 (PC aa C36:2) |
| Lysophosphatidylcholine with acyl residue C18:0 (lysoPC a C18:0) | Phosphatidylcholine with diacyl residue sum C36:3 (PC aa C36:3) |
| Lysophosphatidylcholine with acyl residue C18:1 (lysoPC a C18:1) | Phosphatidylcholine with diacyl residue sum C36:4 (PC aa C36:4) |
| Lysophosphatidylcholine with acyl residue C18:2 (lysoPC a C18:2) | Phosphatidylcholine with diacyl residue sum C36:5 (PC aa C36:5) |
| Lysophosphatidylcholine with acyl residue C20:3 (lysoPC a C20:3) | Phosphatidylcholine with diacyl residue sum C36:6 (PC aa C36:6) |
| Lysophosphatidylcholine with acyl residue C20:4 (lysoPC a C20:4) | Phosphatidylcholine with diacyl residue sum C38:0 (PC aa C38:0) |
| Lysophosphatidylcholine with acyl residue C24:0 (lysoPC a C24:0) | Phosphatidylcholine with diacyl residue sum C38:1 (PC aa C38:1) |
| Lysophosphatidylcholine with acyl residue C26:0 (lysoPC a C26:0) | Phosphatidylcholine with diacyl residue sum C38:3 (PC aa C38:3) |
| Lysophosphatidylcholine with acyl residue C26:1 (lysoPC a C26:1) | Phosphatidylcholine with diacyl residue sum C38:4 (PC aa C38:4) |
| Lysophosphatidylcholine with acyl residue C28:0 (lysoPC a C28:0) | Phosphatidylcholine with diacyl residue sum C38:5 (PC aa C38:5) |
| Lysophosphatidylcholine with acyl residue C28:1 (lysoPC a C28:1) | Phosphatidylcholine with diacyl residue sum C38:6 (PC aa C38:6) |
| Phosphatidylcholine with diacyl residue sum C24:0 (PC aa C24:0) | Phosphatidylcholine with diacyl residue sum C40:1 (PC aa C40:1) |
| Phosphatidylcholine with diacyl residue sum C26:0 (PC aa C26:0) | Phosphatidylcholine with diacyl residue sum C40:2 (PC aa C40:2) |
| Phosphatidylcholine with diacyl residue sum C28:1 (PC aa C28:1) | Phosphatidylcholine with diacyl residue sum C40:3 (PC aa C40:3) |
| Phosphatidylcholine with diacyl residue sum C30:0 (PC aa C30:0) | Phosphatidylcholine with diacyl residue sum C40:4 (PC aa C40:4) |
| Phosphatidylcholine with diacyl residue sum C30:2 (PC aa C30:2) | Phosphatidylcholine with diacyl residue sum C40:5 (PC aa C40:5) |
| Phosphatidylcholine with diacyl residue sum C32:0 (PC aa C32:0) | Phosphatidylcholine with diacyl residue sum C40:6 (PC aa C40:6) |
| Phosphatidylcholine with diacyl residue sum C32:1 (PC aa C32:1) | Phosphatidylcholine with diacyl residue sum C42:0 (PC aa C42:0) |
| Phosphatidylcholine with diacyl residue sum C32:2 (PC aa C32:2) | Phosphatidylcholine with diacyl residue sum C42:1 (PC aa C42:1) |
| Phosphatidylcholine with diacyl residue sum C32:3 (PC aa C32:3) | Phosphatidylcholine with diacyl residue sum C42:2 (PC aa C42:2) |
| Phosphatidylcholine with diacyl residue sum C34:1 (PC aa C34:1) | Phosphatidylcholine with diacyl residue sum C42:4 (PC aa C42:4) |
| Phosphatidylcholine with diacyl residue sum C34:2 (PC aa C34:2) | Phosphatidylcholine with diacyl residue sum C42:5 (PC aa C42:5) |
| Phosphatidylcholine with diacyl residue sum C34:3 (PC aa C34:3) | Phosphatidylcholine with diacyl residue sum C42:6 (PC aa C42:6) |

Figure 5

| Analyte | Analyte |
|---|---|
| Phosphatidylcholine with acyl-alkyl residue sum C30:0 (PC ae C30:0) | Phosphatidylcholine with acyl-alkyl residue sum C38:4 (PC ae C38:4) |
| Phosphatidylcholine with acyl-alkyl residue sum C30:1 (PC ae C30:1) | Phosphatidylcholine with acyl-alkyl residue sum C38:5 (PC ae C38:5) |
| Phosphatidylcholine with acyl-alkyl residue sum C30:2 (PC ae C30:2) | Phosphatidylcholine with acyl-alkyl residue sum C38:6 (PC ae C38:6) |
| Phosphatidylcholine with acyl-alkyl residue sum C32:1 (PC ae C32:1) | Phosphatidylcholine with acyl-alkyl residue sum C40:1 (PC ae C40:1) |
| Phosphatidylcholine with acyl-alkyl residue sum C32:2 (PC ae C32:2) | Phosphatidylcholine with acyl-alkyl residue sum C40:2 (PC ae C40:2) |
| Phosphatidylcholine with acyl-alkyl residue sum C34:0 (PC ae C34:0) | Phosphatidylcholine with acyl-alkyl residue sum C40:3 (PC ae C40:3) |
| Phosphatidylcholine with acyl-alkyl residue sum C34:1 (PC ae C34:1) | Phosphatidylcholine with acyl-alkyl residue sum C40:4 (PC ae C40:4) |
| Phosphatidylcholine with acyl-alkyl residue sum C34:2 (PC ae C34:2) | Phosphatidylcholine with acyl-alkyl residue sum C40:5 (PC ae C40:5) |
| Phosphatidylcholine with acyl-alkyl residue sum C34:3 (PC ae C34:3) | Phosphatidylcholine with acyl-alkyl residue sum C40:6 (PC ae C40:6) |
| Phosphatidylcholine with acyl-alkyl residue sum C36:0 (PC ae C36:0) | Phosphatidylcholine with acyl-alkyl residue sum C42:0 (PC ae C42:0) |
| Phosphatidylcholine with acyl-alkyl residue sum C36:1 (PC ae C36:1) | Phosphatidylcholine with acyl-alkyl residue sum C42:1 (PC ae C42:1) |
| Phosphatidylcholine with acyl-alkyl residue sum C36:2 (PC ae C36:2) | Phosphatidylcholine with acyl-alkyl residue sum C42:2 (PC ae C42:2) |
| Phosphatidylcholine with acyl-alkyl residue sum C36:3 (PC ae C36:3) | Phosphatidylcholine with acyl-alkyl residue sum C42:3 (PC ae C42:3) |
| Phosphatidylcholine with acyl-alkyl residue sum C36:4 (PC ae C36:4) | Phosphatidylcholine with acyl-alkyl residue sum C42:4 (PC ae C42:4) |
| Phosphatidylcholine with acyl-alkyl residue sum C36:5 (PC ae C36:5) | Phosphatidylcholine with acyl-alkyl residue sum C42:5 (PC ae C42:5) |
| Phosphatidylcholine with acyl-alkyl residue sum C38:0 (PC ae C38:0) | Phosphatidylcholine with acyl-alkyl residue sum C44:3 (PC ae C44:3) |
| Phosphatidylcholine with acyl-alkyl residue sum C38:1 (PC ae C38:1) | Phosphatidylcholine with acyl-alkyl residue sum C44:4 (PC ae C44:4) |
| Phosphatidylcholine with acyl-alkyl residue sum C38:2 (PC ae C38:2) | Phosphatidylcholine with acyl-alkyl residue sum C44:5 (PC ae C44:5) |
| Phosphatidylcholine with acyl-alkyl residue sum C38:3 (PC ae C38:3) | Phosphatidylcholine with acyl-alkyl residue sum C44:6 (PC ae C44:6) |

Figure 6

| | |
|---|---|
| (PC aa C42:0/PC ae C44:6) and (PC ae C44:6/PC aa C42:0) | [Phe/(PC ae C38:3/PC aa C28:1)] |
| (PC ae C 42:1/PC aa C40:4) and (PC aa C40:4/PC ae C42:1) | [Ala/(PC ae C36:1PC aa C28:1)] |
| (PC aa C28:1/SM C16:0) and (SM C16:0/PC aa C28:1) | [Glu/(PC ae C40:3/PC aa C28:1)] |
| [Hex/(Arg/Cit)/(C12:1/PC ae C44:3)] | [(Gly/PC aa C40:1)/(C10/C10:1)] |
| (Fumarate/Glutamine) and (Glutamine/Fumarate) | [Glu/(PC ae C38:2/PC aa C28:1)] |
| (Symmetric Dimethylated Arginine/Arginine) (Arginine/Symmetric Dimethylated Arginine) | [Glu/(PC ae C38:1PC aa C28:1)] |
| (Thr/SDMA) and (SDMA/Thr) | [(PC ae C38:3/PC aa C28:1)/(Ser/PC ae C32:1)] |
| (Thr/PC ae C40:2) and (PC ae C40:2/Thr) | [Glu/(PC ae C38:1/SM OH C14:1)] |
| (SDMA/Creatinine) and (Creatinine/SDMA) | [(PC ae C38:1/PC aa C28:1)/(Ser/C14:1)] |
| [(Thr/PC ae C40:2)/(SDMA/PC ae C44:6)] | [(PC ae C38:3/PC aa C28:1)/(Ser/C14:1)] |
| [(Thr/PC ae C40:2)/PC ae C42:5/SDMA)] | [(PC ae C38:2/PC aa C28:1)/(Ser/C14:1) |
| {[(Thr/PC ae C40:2)/(PC ae C42:5/SDMA)]/C3-OH} | [(Ala/(PC ae C38:3/PC aa C28:1)] |
| (PC aa C36:2/SM C16:0) | [(Taurine/Glycine)/PC aa C34:2] |
| [Kyn/(Creat/SDMA)] | (PC ae C38:2/PC ae C36:2) |
| {(Kyn/Trp)/[(PC ae C30:2/PC ae C42:5)/(Phe/Gln)]} | (Taurine/PC aa C34:2) |
| {PC ae C40:4/[(PC ae C30:2/PC ae C42:5)/(Phe/Gln)]} | [(C16-OH/C162-OH)/(lysoPC a C16:0/D9 Arac PC ae)] |
| APO.3/[(PC ae C30:2/PC ae C42:5)/(Phe/Gln)] | (PC aa C32:2/SM C16:0) |
| APO.31/[(PC ae C30:2/PC ae C42:5)/Phe/Gln] | [PC ae C32:1/(SM C16:0/PC ae C36:1)] |
| {(Kyn/Leu)/[(PC ae C30:2/PC ae C42:5)/(Phe/Gln)]} | [(Ser/C18:1)/(PC ae C40:4/C18:2)] |
| {(Leu+Ile)/(Total PC ae/Total PC)] | [(C10/C10:1)/(Ser/PC ae C40:4)] |
| [C3:1/(Thr/SDMA)] | [Glu/(PC ae C40:3/PC ae C44:5)] |
| [(Orn/Arg)/(Thr/SDMA)] | [Ala/(PC ae C38:3PC ae C38:4)] |
| [C4:1/(Thr/SDMA)] | (Val/Phe) |
| [(SDMA/Thr)/(D6 SM/D9)] | [PC aa C36:6/(SM (OH) C24:1/SM (OH) C22:2)] |

Figure 7A

| | |
|---|---|
| [(Arg/SDMA)/(Thr/PC ae C42:0)] | [Glu/(PC ae C38:3/PC aa C28:1)] |
| [Hex/(SDMA/Thr)] | [Asp/(PC ae C38:1/PC aa C28:1)] |
| [C5/(Thr/SDMA)] | [(PC aa C42:0/PC ae C44:6)/PC aa C38:5/lysoPC a C16:1)] |
| [(Orn/Arg)/(Thr/SDMA)] | (Taurine/Gln) and (Gln/Taurine) |
| [C12-DC/(Thr/SDMA)] | [Taurine/(Gln/Glu)] |
| (PC aa C36:3/PC aa C36:4) | (Asp/Arg) and (Arg/Asp) |
| (C12/C10) | [(PC ae C32:1/(PC ae C44:6/PC ae C44:4)] |
| (PC aa C36:3/PC aa C36:4) | [(Taurine/Glycine)/PC aa C34:2] |
| (Thr/Ser) | (C18:1/C0) |
| (Val/C5) | (Gln/Trp) and (Trp/Gln) |
| (PC aa C36:2/SM C16:0) | (C14:1-OH/C16:1) |
| (C14:1-OH/C10) | [(C16:1/C16:2)/(C10:1/C12:1)] |
| (PC aa C36:2/SM C16:0) | [(C16:1/C16:2)/(C5-DC/C16:1)] |
| Total lysophosphatidylcholines | (C10:1/C12:1) |
| Sum of Structural Lipids (Phosphatidylcholines + Sphingomielins) | (C16:1/C16:2) |
| Sum of acyl-acyl phosphatidylcholines | [(C16:1/C16:2)/(C5:1-DC/C16:1)] |
| Sum of acyl-alkyl phosphatidylcholines | [(PC aa C3:23/PC ae C30:2)/C12-DC] |
| (C5-DC/C12) | (C5-DC/C16:1) |
| (C5-DC/C8) | [(C10:1/C12:1)/AcylC-OH] |
| (C16:1/C16:2) | [(C16:1/C16:2-OH)/(C10:1/C12:1)] |
| Sum of Dicarboxylic Acylcarnitines | [(C10:1/C12:1)/C16:1] |
| (Phe/Trp) and (Trp/Phe) | [(C5:1-DC/C16:1)/(PC ae C30:2/PC ae C40:1)] |
| (lysoPC a C17:0/PC ae C30:0) | (C5-M-DC/C16:1) |
| [(lysoPC a C17:0/PC ae C30:2)/C16:1-OH] | (C12-DC/C16:2-OH) |
| (C12/C10) | [(C5:1-DC/C16:1)] |
| (C16:2-OH/C16-OH) and (C16-OH/C16:2-OH) | [(C10:1/C12:1)/(PC ae C30:2/PC ae C40:1)] |
| [C14/(lysoPC a C17:0/PC aeC30:2)] | (C4/C0) and (C0/C4) |
| (PC aa C36:3/PC aa C36:4) and (PC aa C36:4/PC aa C36:3) | (C4/Trp) and (Trp/C4) |
| (SM C24:1/PC ae C36:5)/(SM OH C22:1/PC ae C30:1) | [(PC ae C32:1/(PC ae C44:6/PC ae C44:4)] |

Figure 7B

| | | |
|---|---|---|
| 40 acylcarnitines (ACs) | Pyruvate | Aromatic amino acids (Hist +Tyr+trp+Pne) (Arom AA) |
| 21 amino acids (AAs) | Oxaloacetate | Glutaminolytic amino acids (Ala+Asp+Glu) |
| 19 biogneic amines (BA) | Alpha ketoglutarate | Groups of acycarnitines as total (AC), C2+C3, C16+C18, C16+C18.1 and C16-OH+C18:1-OH |
| Sum of Hexoses (Hex) | Fumurate | Total lysophosphatidylcholines (Total LPC) |
| 76 phosphotidylcholines (PCs) | Succinate | Total Acyl-acyl (Totla PC aa) |
| 14 lysophosphotiylcholines (LPCs) | Essential amino acids (Essentila AAs) | Total Acyl-alkyl (Total PC ea) |
| 15 sphingomyelins (SMs) | Non-essential amino acids (non-Essential AAs) | Total sphingomyelins (Total SMs) |
| Glycerophospholipids (GPLs) | Glucogenic amino acids (Ala+Gly+Ser)) (Gluc AA) | Sum of total (LPC+PC aa+PC ae + SM) (Structural lipids) |
| Lactate | Branched chain amino acids (Leu+Ile+Val) (BCAA) | Sums of Saturated, Mono-unsaturated and Polyunsaturated structural lipids |

Figure 8

| |
|---|
| Elongase and Desaturase Activity: |
| Desaturase 9 [(PCaeC36:1 + PC ae C38:1 + PC ae C42:1) / (PC ae C42:0)] |
| Desaturase 6 [(PC ae C44:6 + PC ae C44:5 + PC ae C42:5 + PC ae C40:6 + PC ae C40:5 + PC ae C38:6 + PC ae C38:5 + PC ae C36:5) / (PC ae C36:1 + PC ae C38:1 + PC ae C42:1)] |
| Liver Function: |
| (leucine+isoleucine+valine/(tyrosine+phenylalanine) |
| (Val/Phe, Xleu/Phe) |
| Indicators of isovaleric acidemia, tyrosinemia, urea cycle deficiency and disorders of ß-oxidation: |
| Valerylcarnitine/butyrylcarnitine (C5/C4), tyrosine to serine (Tyr/Ser), glycine to alanine and glutamine (Gly/Ala, Gly/Gln) and lactate to pyruvate (Lac/Pyr) |
| Very long-chain acyl-CoA dehydrogenase (VLCAD) and type 2 carnitine-palmitoyl transferase (CPT-2) deficiencies: |
| (C16+C18:1/C2), (C14:1/C4), (C14:1-OH/C9), (C14/C9), (C14:1/C9) and to the elongation of very-long-chain-fatty acids (ELOVL2) (PC aa C40:3/PC aa C42:5) |
| ROS-mediated protein modifications as well as to systemic arginine methylation status: |
| Levels of methionine sulfoxide (Met-SO) alone or in combination to unmodified methionine (Met-SO/Met) as well as symmetric (SDMA), asymmetric (ADMA) and total dimethylation of argine residues (Total DMA) |
| Insulin-MYC-related activity: |
| (Glucose/Ser, Glucose/Gly and Glucose/Ala) |
| MYC-responsive enzymes: |
| Arginine methyltransferases (ADMA, ADMA/Arg, SDMA, SDMA/Arg and Total DMA, Total DMA/Arg), ornithine decarboxylase (Glu, Glu/Orn, Pro, Pro/Orn, Orn, Orn/Arg, Putrescine, Putrescine/Orn, Spermidine, Spermidine/Putrescine, Spermine and Spermine/Spermidine), alanine aminotransferase (Ala), (Ala/Glu), aspartate aminotransferase (Asp) and (Asp/Glu), glutaminase (Glu), (Gln/Glu), [(Glu+Asp+Ala)/Gln], [(Gln/Glu)/Asp], (Glu/Glucose)/(Ala/Glu) and [(Glu/Gln)/Glucose]/(Ala/Glu) |
| Glutamate Pulling Effect: |
| GDH activity |
| Glycolysis-related phosphoglycerate dehydrogenase (PHGDH) and glucokinase regulator (GCKR) activities: |
| (Ser/C2, Ser/Gln, Ser/Thr) |
| (PC aa C42:0/PC ae C32:3, PC aa C32:2/PC ae C34:2) |
| Glutaminolytic activity: |
| (Gln/Glu) |
| [(Gln/Glu)/Asp] |
| [(Ser/C2)/(Gln/Glu)] |
| [(Ser/C2)/(Gln/Glu)/Asp] |
| [(Ser/C2)/(Gln/Glu)/Asp] |
| [(PC aa C32:2/PC ae C34:2)/(Gln/Glu)] |
| [(PC aa C32:2/PC ae C34:2)/(Gln/Glu)/Asp] |

Figure 9

| Likelihood Ratios (LR) | Interpretation |
|---|---|
| >10 | Large and often conclusive increase in the likelihood of disease |
| 5-10 | Moderate increase in the likelihood of disease |
| 2-5 | Small increase in the likelihood of disease |
| 1-2 | Minimal increase in the likelihood of disease |
| 1 | No change in the likelihood of disease |
| 0.5-1.0 | Minimal decrease in the likelihood of disease |
| 0.2-0.5 | Small decrease in the likelihood of disease |
| 0.1-0.2 | Moderate decrease in the likelihood of disease |
| <0.1 | Large and often conclusive decrease in the likelihood of disease |

Figure 10

| Characteristics | Remarks |
|---|---|
| Highly specific | Detectable only in one tumor type |
| Highly sensitive | Non-detectable in physiological or benign disease states |
| Long lead-time | Sufficient time for alteration of natural course of disease |
| Levels correlate with tumor burden | Prognostic and predictive utility |
| Short half-life | Frequent serial monitoring of the marker levels after 5-6 half lives |
| Simple and cheap test | Applicability as screening test |
| Easily obtainable specimens | Acceptability by target population |

Figure 11

| Positive | |
|---|---|
| Ovary Cancer (OvCA) | 64 |
| False negative | 1 |
| Negative | |
| False positive | 35 |
| Controls (Cnt) | 1001 |
| Sensitivity | 98.46% |
| Specificity | 96.62% |
| Positive predictive value | 64.65% |
| Negative predictive value | 99.90% |

| Ovarian Cancer Equation Core | Enhancer (Single Metabolites) | Enhancer (Ratios) | Equation Core with Enhacers |
|---|---|---|---|
| (C5:1/C5:1-DC) | C12-DC | (C18:1/Asp) | [C12-DC/((C5:1/C5:1-DC)]* |
| | C6:1 | (C18:1/lysoPC a C17:0) | [C12-DC/((C5:1/C5:1-DC)]/C6:1 |
| | Aspartate | (C18:1/lysoPC a C18:0) | [C12-DC/((C5:1/C5:1-DC)]/Asp] |
| | lysoPC a C28:1 | (C18:1/lysoPC a C20:3) | [C12-DC/((C5:1/C5:1-DC)]/lysoPC a C28:1 |
| | PC aa C40:1 | (C18:1/PC aa C34:4) | [C12-DC/((C5:1/C5:1-DC)]/lysoPC a C40:1 |
| | PC aa C42:5 | [(Trp/C18:1)/lysoPC a C17:0)/PC ae C36:3] | [C12-DC/((C5:1/C5:1-DC)]/PC aa C42:5 |
| | PC aa C42:4 | [(C16:1/lysoPC a C17:0)/PC aa C34:2] | [C12-DC/((C5:1/C5:1-DC)]/PC aa C42:4 |
| | PC ae C40:4 | (C18:1/lysoPC a C17:0) | [C12-DC/((C5:1/C5:1-DC)]/PC ae C40:4 |
| | PC aa C40:3 | [(C18:1/lysoPC a C16:0)/AA] | [C12-DC/((C5:1/C5:1-DC)]/PC aa C40:3 |
| | PC aa C42:6 | (C18:1/lysoPC a C16:0) | [C12-DC/((C5:1/C5:1-DC)]/PC aa C42:6 |
| | PC ae C38:3 | [(C18:1/lysoPC a C18:0)/dAA] | [C12-DC/((C5:1/C5:1-DC)]/PC ae C38:3 |
| | PC ae C42:2 | [C18.1/PC aa C34:4)/AA] | [C12-DC/((C5:1/C5:1-DC)]/PC ae C42:2 |
| | PC ae C38:2 | [((C18:1/lysoPC a C17:0)/PC aa C34:2)/AA] | [C12-DC/((C5:1/C5:1-DC)]/PC ae C38:2 |
| | PC ae C42:1 | (C18:1/PC aa C34:4)/His] | [C12-DC/((C5:1/C5:1-DC)]/PC ae C42:1 |
| | lysoPC a C17:0 | [(C18:1/PC ae C36:3)/AA] | [C12-DC/((C5:2/C5:3-DC)]/lysoPC a C17:0 |
| | | (C18.1/PC ae C36:3)/Trp) | [(C18:1/Asp]/(C5.1/C5:1-DC)]* |
| | lysoPC a C16:1 | [(C18.1/PC ae C34:4)/Trp) | (C5:1/C5:1-DC)][(C18:1/PC ae C36:3)/Trp) |
| | PC ae C30:2 | (C18:1/PC ae C16:1) | (C5:1/C5:1-DC)][((C18:1/lysoPC a C17:0)/PC aa C34:4)/AA) |
| | Triptophan | (C18:1/PC ae C40:1) | (C5:1/C5:1-DC)/(C18:1/PC ae C34:4)/Trp) |
| | Histidine | [[((C18:1/lysoPC a C17:0)/PC aa C34:4)/AA] | (C5:1/C5:1-DC)/[((C18:1/lysoPC a C17:0)/PC aa C17:0)/AA) |
| | | [[(C18:1/lysoPC a C17:0)/lysoPC a C17:0)/AA] | (C5:1/C5:1-DC)/[((C18:1/lysoPC a C17:0)/lysoPC a C17:0)/AA] |
| | | [(C18:1/PC ae C36:2)/His) | (C5:1/C5:1-DC)/[(C18:1/PC ae C36:2)/His] |
| | | Aromatic Aminoacids (AA) (His+Trp+Phe+Tyr) | (C5:1/C5:1-DC)/[(C18:1/PC ae C36:3)/Trp)/AA) |
| | | [Orn/(AspdC18:1)]* | [Orn/(AspdC18:1)]/(C5:1/C5:1-DC] |
| | | [(Orn/Arg)/Trp]* | [(Orn/Arg)/Trp]/(C5:1/C5:1-DC) |

Figure 15

| Positive | |
|---|---|
| True positive | 85 |
| False negative | 1 |
| | |
| Negative | |
| False positive | 13 |
| True negative | 800 |
| | |
| Sensitivity | 98.84% |
| Specificity | 98.40% |
| Positive predictive value | 86.73% |
| Negative predictive value | 99.88% |

| Colon Cancer Equation Core | Enhacer Single Metabolites | Equation Core with Enhacers |
|---|---|---|
| (C16:1/PC aa C34:2) | C5:1-DC | [(C16.1/PC aa C34:2)/C5:1-DC] |
| | C16:1 | {SM C20:2/[(C16:1/PC aa C34:2)/C5:1-DC]}* |
| | SM C20:2 | {SM OH C16:1/[(C16:1/PC aa C34:2)/C5:1-DC]}* |
| | SM OH C16:1 | {SM OH C14:1/[(C16:1/PC aa C34:2)/C5:1-DC]}* |
| | SM OH C14:1 | |

| Positive | |
|---|---|
| True positive | 10 |
| False negative | 0 |

| Negative | |
|---|---|
| False positive | 15 |
| True negative | 709 |

| | |
|---|---|
| Sensitivity | 100.00% |
| Specificity | 97.93% |
| Positive predictive value | 40.00% |
| Negative predictive value | 100.00% |

| Pancreas Cancer Equation Cores | Enhancer Metabolite Ratios | Equation Core with Enhancers 1 | Equation Core with Enhancers 2 |
|---|---|---|---|
| (C3:1/C12-DC) | (Asp/C5-DC) | (Asp/C5-DC)/(C3:1/C12-DC) | (Asp/C5-DC)/(C6:1/C12-DC) |
| (C6:1/C12-DC) | (Asp/C16:1) | (Asp/C16:1)/(C3:1/C12-DC) | (Asp/C16:1)/(C6:1/C12-DC) |
| | (C5-DC/C12) | (C5-DC/C12)/(C3:1/C12-DC) | (C5-DC/C12)/(C6:1/C12-DC) |
| | (lysoPC a C17:0/C12-DC*) | (lysoPC a C17:0/C12-DC*)/(C3:1/C12-DC) | (lysoPC a C17:0/C12-DC*)/(C6:1/C12-DC) |
| | (C5-DC/C16:2-OH) | (C5-DC/C16:2-OH)/(C3:1/C12-DC) | (C5-DC/C16:2-OH)/(C6:1/C12-DC) |
| | (C12-DC/lysoPC a C17:0*) | (C12-DC/lysoPC a C17:0*)/(C3:1/C12-DC) | (C12-DC/lysoPC a C17:0*)/(C6:1/C12-DC) |
| | (Asp/Gln) | (Asp/Gln)/(C3:1/C12-DC) | (Asp/Gln)/(C6:1/C12-DC) |
| | (SM C16:0/PC ae C38:3) | (SM C16:0/PC ae C38:3)/(C3:1/C12-DC) | (SM C16:0/PC ae C38:3)/(C6:1/C12-DC) |
| | (C0/lysoPC a C26:1) | (C0/lysoPC a C26:1)/(C3:1/C12-DC) | (C0/lysoPC a C26:1)/(C6:1/C12-DC) |
| | (C0/C16:1-OH) | (C0/C16:1-OH)/(C3:1/C12-DC) | (C0/C16:1-OH)/(C6:1/C12-DC) |
| | (SM C16:0/PC ae C32:1) | (SM C16:0/PC ae C32:1)/(C3:1/C12-DC) | (SM C16:0/PC ae C32:1)/(C6:1/C12-DC) |
| | (SM C16:0/PC ae C36:1) | (SM C16:0/PC ae C36:1)/(C3:1/C12-DC) | (SM C16:0/PC ae C36:1)/(C6:1/C12-DC) |
| | (PC aa C30:2/lysoPC a C16:1) | (PC aa C30:2/lysoPC a C16:1)/(C3:1/C12-DC) | (PC aa C30:2/lysoPC a C16:1)/(C6:1/C12-DC) |
| | (SM C16:0/lysoPC a C16:1) | (SM C16:0/lysoPC a C16:1)/(C3:1/C12-DC) | (SM C16:0/lysoPC a C16:1)/(C6:1/C12-DC) |
| | (SM C16:0/PC ae C32:2) | (SM C16:0/PC ae C32:2)/(C3:1/C12-DC) | (SM C16:0/PC ae C32:2)/(C6:1/C12-DC) |
| | (SM OH C24:1/PC ae C40:5) | (SM OH C24:1/PC ae C40:5)/(C3:1/C12-DC) | (SM OH C24:1/PC ae C40:5)/(C6:1/C12-DC) |
| | (SM OH C24:1/PC ae C38:3) | (SM OH C24:1/PC ae C38:3)/(C3:1/C12-DC) | (SM OH C24:1/PC ae C38:3)/(C6:1/C12-DC) |

Figure 23

METABOLOMIC SIGNATURES FOR PREDICTING, DIAGNOSING, AND PROGNOSING VARIOUS DISEASES INCLUDING CANCER

RELATED APPLICATIONS DATA

This application claims priority to several provisional patent applications, including Ser. No. 62/685,275, which was filed on Jun. 14, 2018, Ser. No. 62/714,650, which was filed on Aug. 3, 2018, Ser. No. 62/830,389, which was filed on Apr. 6, 2019, and Ser. No. 62/838,683, which was filed on Apr. 25, 2019, the subject matter of which are incorporated by reference herein in their entirety.

BACKGROUND OF THE INVENTION

1. Field of the Invention

The present invention relates to new biomarkers for assessing various diseases, and in particular to the use of absolute quantification of annotated metabolites by mass spectrometry to identify certain biomarkers and derivatives thereof (i.e., signatures) that can be used to screen for, diagnose, predict, prognose, and treat various diseases, including, but not limited to breast cancer, ovarian cancer, colorectal cancer, pancreatic cancer, and acute graft-versus-host disease, to name a few.

2. Description of Related Art

MYC is a member of a family of regulator genes and proto-oncogenes that code for transcription factors. As such, MYC leads to the increased expression of many genes, some of which are involved in metabolic reprogramming and cell proliferation, contributing to the formation of cancer. In fact, it is largely accepted that in order to meet cancer biochemical requirements tumor metabolism become addicted to local MYC oncogene activation. However, studies performed by the inventors suggest that in situ tumor gene activation should be seen as a confined replication of a previously existent systemic inborn-like condition already detectable in cancer-free participants at elevated risk of cancer development.

The latter is the effect of variable elevated levels of insulin resistance over patients exhibiting phenotypic mild deficiencies known as Fatty Acids Oxidation Defects (FAOD) exhibiting energy production deficiencies due to $\beta$-oxidation impairments followed by hypoglycemia due to insufficiencies in gluconeogenesis pathways.

Indeed, in these patients, high insulin levels systemically activate MYC proto-oncogene inducing glutaminolysis, glycolysis, $\Delta 9$-stearoyl-CoA desaturase (SCD) activity and inhibition of liver gluconeogenesis. When added to prominent blood levels of very-long chain acylcarnitines, lactate, fumarate and succinate, the final phenotypic scenario is highly suggestive of peroxisome and/or mitochondrial $\beta$-oxidation dysfunctions.

As an example, in studies conducted by the inventors, the phenotypic quantification of this MYC-induced "ambiance" was able to accurately discriminate between breast cancer patients from controls at AUC=0.994 (95% CI:0.978-1), Sensitivity=98.72%, Specificity=98.26%, PPV=98.09%, NPV=98.83%, Average Accuracy=0.982 (100-fold cross validations) and Predictive Accuracy Statistics p<9.2e-06 (1000 permutations) irrespective to disease stage, histology, intrinsic subtype classification, BMI, menopausal status, age, and patient's continental geographic localization (South American or European Continent).

As a proof-of-principle of the direct connections to stemness and cancer, the phenotypic metabolic deviations identified in the studies were highly correlated to human embryo metabolism and exhibited elevated predictive capabilities of chemotherapy response and outcomes of survival. The validation process of these findings, besides confirmation in independent cohorts, were also present, to a considerable extend, in other malignancies of glandular origin.

This research provides biochemical support to the hypothesis of cancer as a physical epiphenomenon of a preexisting MYC-induced systemic condition. In addition to ratifying local malignant lipidogenesis, glutaminolysis and glycolysis as major drivers in cancer, this study is one of the first to provide largely validated biochemical support to the hypothesis of cancer as a physical epiphenomenon of a systemic, preexistent, stemmness-like MYC-related condition, that according to results of the studies, closely resemble specific inborn errors of metabolism.

In doing so, the inventors relied on targeted quantitative metabolomics, which is the absolute quantitative measurement, by liquid chromatography followed by tanden mass spectrometry (LC-MS/MS), of low molecular weight compounds covering key biochemically active metabolites belonging to the whole range of pathways related to biosynthesis, signaling and catabolism of (i) structural and non-structural lipids, (ii) amino acids, (iii) biogenic amines, and (iv) components of intermediary metabolisms.

Considered as the gold standard of quantification, the very recent popularity of clinical mass spectrometry can be attributed to the high specificity, accuracy and reliability due to the direct analysis of ions that constitute that specific analyte, without the risk of cross reactivity as described for direct antibody assay detection.

The capability to analyze large arrays of annotated metabolites extracts biochemical information reflecting true functional end-points of overt biological events while genomics, transcriptomics and proteomics technologies, though highly valuable, merely indicate the potential cause for phenotypic response, and therefore cannot necessarily predict drug effects, toxicological response or disease states at the phenotype level unless functional validation is added. Metabolomics bridges this information gap by depicting functional information, since metabolite differences in biological fluids and tissues provide the closest link to the various phenotypic responses.

Needless to say, such changes in the biochemical phenotype are of direct interest to pharmaceutical, biotech and health industries once appropriate technology allows the cost-efficient mining and integration of this information. In general, phenotype is not necessarily predicted by genotype. The gap between genotype and phenotype is spanned by many biochemical reactions each with individual dependencies to various influences, including drugs, nutrition and environmental factors.

In this chain of biomolecules from the genes to phenotype, metabolites are the quantifiable molecules with the closest link to phenotype. Studies conducted by the inventors show that many phenotypic and genotypic states, such as a toxic response to a drug or disease prevalence are predicted by differences in the concentrations of functionally relevant metabolites within biological fluids and tissue.

Thus, in light of the foregoing, it would be advantageous to develop a system and method that uses targeted metabolomics, or absolute quantification of annotated metabolites by mass spectrometry, to identify certain biomarkers and derivatives thereof, such as ratios, etc. (i.e., "signatures") that can be used to screen for, diagnose, predict, prognose, and treat various diseases.

SUMMARY OF THE INVENTION

The present invention provides a system and method for using new biomarkers to assess individual diseases. Preferred embodiments of the present invention include use of absolute quantification of annotated metabolites by mass spectrometry to identify certain biomarkers and derivatives thereof (i.e., "signatures"), which can then be used to screen for, diagnose, predict, prognose, and treat various diseases.

In one embodiment of the present invention, targeted metabolomic analysis of plasma and/or tissue samples are performed. Absolute quantification (μmol/L) of blood metabolites is achieved by targeted quantitative profiling of certain (e.g., up to 186) annotated metabolites by electrospray ionization (ESI) tandem mass spectrometry (MS/MS).

In one embodiment of the present invention, a targeted profiling scheme is used to quantitatively screen for fully annotated metabolites using multiple reaction monitoring, neutral loss and precursor ion scans. Quantification of metabolite concentrations is performed, resulting in at least one file that includes (i) sample identification, (ii) metabolite names (e.g., up to 186), and (iii) concentrations (e.g., μmol/L of plasma).

For metabolomic data analysis, log-transformation is then applied to all quantified metabolites to normalize the concentration distributions and provided to software for comparing (e.g., mapping, plotting, etc.) to previously known "signatures." In one embodiment, signature identification may involve uploading the data into MetaboAnalyst 3.0 (a web-based analytical pipeline) and ROCCET (a Receiver Operating Characteristic Curve Explorer & Tester) for the generation of uni and multivariate ROC (Receiver Operating Characteristic) curves obtained through SVM (Support Vector Machine), PLS_DA (Partial Least Squares-Discriminant Analysis), and Random Forests as well as Logistic Regression Models.

In certain embodiments of the present invention, there are up to 186 annotated metabolites that are quantified for comparision, including 40 acylcanitines (ACs), 21 amino acids (AAs), 19 biogenic amines (BA), sum of hexoses (Hex), 76 phosphatidylcholines (PCs), 14 lyso-phosphatidylcholines (LPCs) and 15 sphingomyelins (SMs). Glycerophospholipids were further differentiated with respect to the presence of ester (a) and ether (e) bonds in the glycerol moiety, where two letters denote that two glycerol positions are bound to a fatty acid residue (aa=diacyl, ae=acyl-alkyl), while a single letter indicates the presence of a single fatty acid residue (a=acyl or e=alkyl). Samples may also be analyzed for energy metabolism metabolites, including lactate, pyruvate/oxaloacetate, alpha ketoglutarate, fumarate and succinate.

In addition to individual metabolite quantification, groups of metabolites related to specific functions were assembled as ratios based on previous observation that the proportions between metabolite concentrations can strengthen the association signal and at the same time provide new information about possible metabolic pathways. As discussed below, these ratios are (at least in certain embodiments) extremely important aspects of a disease's "signature," and can, in and of themselves, indicate the presence or likelihood of a particular disease, the patient's prognosis, and available treatments.

In other embodiment, other groupings were also found to be important, including groups of amino acids (AA) that are computed by summing the levels of AAs belonging to certain families or chemical structures depending on their functions, such as the sum of: 1) essential amino acids (essential AA); 2) non-essential amino acids (non-essential AA); 3) glucogenic (Ala+Gly+Ser) amino acids (Gluc AA); 4) branched-chain (Leu+Ile+Val) amino acids (BCAA); 5) Aromatic (His+Tyr+Trp+Phe) amino acids (Arom AA); 6) glutaminolytic derivatives (Ala+Asp+Glu); and 7) the sum of total amino acids.

Groups of acylcarnitines (AC), important to evaluate mitochondrial function, may also be computed by summing total acylcarnitines (AC), C2+C3, C16+C18, C16+C18:1 and C16-OH+C18:1-OH). Groups of lipids, important to evaluate lipid metabolism, may also be analyzed by summing: 1) total lysophosphatidylcholines (total LPC); 2) total acyl-acyl; and 3) total acyl-alkyl phosphatidylcholines (total PC aa and total PC ae, respectively); 4) total sphingomielins (total SM); and 5) sum of total (LPC+PC aa+PC ae+SM) lipids (structural lipids).

Proportions among sums of saturated, monounsaturated and polyunsaturated structural lipids may also be assembled as proxies to estimate elongases and desaturases activities towards ether lipids: 1) Desaturase 9 [(PC ae C36:1+PC ae C38:1+PC ae C42:1)/(PC ae C42:0)], Desaturase 6 [(PC ae C44:6+PC ae C44:5+PC ae C42:5+PC ae C40:6+PC ae C40:5+PC ae C38:6+PC ae C38:5+PC ae C36:5)/(PC ae C36:1+PC ae C38:1+PC ae C42:1)].

Clinical indicators of liver metabolism and function may also be obtained by applying either the classical (leucine+isoleucine+valine)/(tyrosine+phenylalanine) or variations (Val/Phe, Xleu/Phe) of the Fischer quotient. Clinical indicators of isovaleric acidemia, tyrosinemia, urea cycle deficiency and disorders of β-oxidation may also be calculated by adopting the ratios of valerylcarnitine to butyrylcarnitine (C5/C4), tyrosine to serine (Tyr/Ser), glycine to alanine and glutamine (Gly/Ala, Gly/Gln) and lactate to pyruvate (Lac/Pyr), respectively. Proxies for enzyme function related to the diagnosis of very long-chain acyl-CoA dehydrogenase (VL-CAD) and type 2 carnitine-palmitoyl transferase (CPT-2) deficiencies may also be achieved by assembling the ratios (C16+C18:1/C2), (C14:1/C4), (C14:1-OH/C9), (C14/C9), (C14:1/C9) and to the elongation of very-long-chain-fatty acids (ELOVL2) (PC aa C40:3/PC aa C42:5). Levels of methionine sulfoxide (Met-SO) alone or in combination to unmodified methionine (Met-SO/Met) as well as symmetric (SDMA), asymmetric (ADMA) and total dimethylation of argine residues (Total DMA) may then be quantified to gain access to ROS-mediated protein modifications as well as to systemic arginine methylation status, respectively.

Knowing that liver inhibition of gluconeogenesis is a bona fide insulin-MYC-dependent biochemical reaction, a shift from normal to lower values in the ratio of glucose to glucogenic amino acids (Glucose/Ser, Glucose/Gly and Glucose/Ala) after insulin administration, may be adopted as a measurement of insulin-MYC-related activity.

The same procedure may then be applied to other MYC-responsive enzymes as follows: arginine methyltransferases (ADMA, ADMA/Arg, SDMA, SDMA/Arg and total DMA, total DMA/Arg), ornithine decarboxylase (Glu, Glu/Orn, Pro, Pro/Orn, Orn, Orn/Arg, Putrescine, Putrescine/Orn, Spermidine, Spermidine/Putrescine, Spermine and Spermine/Spermidine), alanine am inotransferase (Ala), (Ala/Glu), aspartate aminotransferase (Asp) and (Asp/Glu), glutaminase (Glu), (Gln/Glu), [(Glu+Asp+Ala)/Gln], [(Gln/Glu)/Asp], (Glu/Glucose)/(Ala/Glu) and [(Glu/Gln)/Glucose]/(Ala/Glu).

The latter two ratios are related to the "glutamate pulling effect," which is defined as the hypoglycemia-induced up-regulation in the deaminated, rather than transaminated, production of glutamate through insulin-MYC-dependent glutamate dehydrogenase (GDH) stimulation of glutaminolysis with consequent increased amounts of net keto acids to anaplerosis.

The ratios of (Ser/C2, Ser/Gln, Ser/Thr) and of (PC aa C42:0/PC ae C32:3, PC aa C32:2/PC ae C34:2) as proxies for glycolysis-related phosphoglycerate dehydrogenase (PHGDH) and glucokinase regulator (GCKR) activities may also be considered. The later inhibits glucokinase activity in liver and pancreas and the former catalyses the rate limiting step of serine biosynthesis.

In parallel, and assuming the ratio values of glutamine to glutamate (Gln/Glu) and to aspartate [(Gln/Glu)/Asp], as proxys for glutaminolytic activity, the ratios [(Ser/C2)/(Gln/Glu)], [(Ser/C2)/(Gln/Glu)/Asp], [(PC aa C32:2/PC ae C34:2)/(Gln/Glu)] and [(PC aa C32:2/PC ae C34:2)/(Gln/Glu)/Asp] may be assembled as theoretical equations to gain access to the balance between glycolysis and glutaminolysis.

It should be appreciated that with respect to the foregoing metabolites and sets thereof (e.g., summation, ratio, etc.), certain ones may be critical to analyzing a particular disease, whereas others may be less important. Thus, provided below are metabolites and/or sets thereof that are critical (i.e., most important) to individual signatures. For the sake of brevity, critical aspects of individual signatures for individual disease will be covered in the appropriate sections below.

A more complete understanding of a system and method for using new biomarkers to assess individual diseases will be afforded to those skilled in the art, as well as a realization of additional advantages and objects thereof, by a consideration of the following detailed description of the preferred embodiment. Reference will be made to the appended sheets of drawings, which will first be described briefly.

BRIEF DESCRIPTION OF THE DRAWINGS

FIGS. 2-6 provide a list of analytes, including their abbreviations, that are considered metabolites (or sets thereof) used in certain embodiments of the present invention;

FIGS. 7A and B provide a list of ratios that have been identified as useful in assessing different types of diseases;

FIG. 8 provides a list of parameters that have been identified as useful in assessing at least ovarian cancer;

FIG. 9 provides a list of ratios that have been identified as useful in assessing at least ovarian cancer;

FIG. 10 provides likelihood ratios, and interpretations thereof, used by the inventors during performance of Statistical Univariate Analysis;

FIG. 11 provides characteristics, and remarks concerning the same, used by the inventors when identifying ideal tumor markers according to Sokoll and Chan;

FIG. 15 provides metabolites and mathematical derivatives thereof (e.g., ratios, etc.) that are used in one embodiment of the present invention to assess (e.g., diagnose, prognose, etc.) ovarian cancer in a patient;

FIG. 23 provides metabolites and mathematical derivatives thereof (e.g., ratios, etc.) that are used in one embodiment of the present invention to assess (e.g., diagnose, prognose, etc.) pancreatic cancer in a patient.

DETAILED DESCRIPTION OF THE PREFERRED EMBODIMENT

Figure 1:
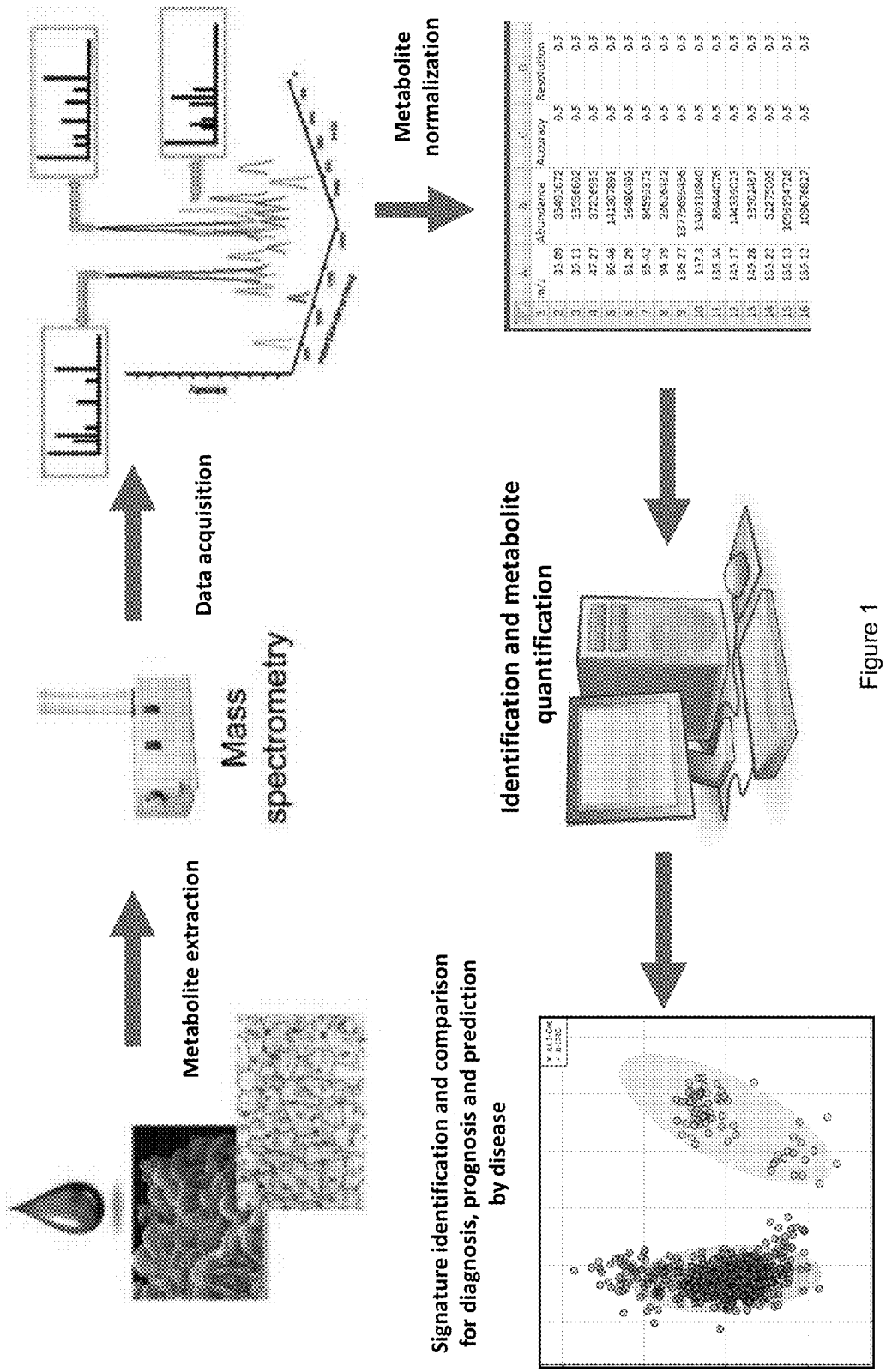
FIG. 1 illustrates a method in accordance with one embodiment of the present invention as to how a metabolic signature for a disease is identified and subsequently used to assess a patient's blood sample as to that disease.

Preferred embodiments of the present invention involve use of targeted metabolomics, or absolute quantification of annotated metabolites by mass spectrometry, to identify never described biomarkers and/or derivatives thereof (e.g., ratios, etc.) (i.e., "signatures") suitable for assessing various diseases, including, but not limited to breast cancer, ovarian cancer, colorectal cancer, pancreatic cancer, and acute graft-versus-host disease, to name a few.

It should be appreciated that while a first disease (e.g., breast cancer) may have a first signature, and a second disease (e.g., ovarian cancer) may have a second, different signature, the method used in identifying each signature is very similar, and in certain instances identical. Thus, while different diseases have been discussed in different sections below, for the sake of brevity, details concerning how a signature is identified and subsequently used to assess a particular disease are equally applicable to other signatures and other diseases unless stated otherwise. For example, details concerning absolute quantification of annotated metabolites by mass spectrometry provided in the breast cancer section applies equally to the ovarian cancer section, as do other details, unless stated otherwise.

It should also be appreciated that a disease may have more than one signature or portions thereof. For example, a first signature may be used for diagnoses, a second signature (or portion of the first signature) may be used for prognoses, etc. It should also be appreciated that while a disease may have more than one signature, there may be individual aspects (e.g., individual metabolites or derivatives thereof) that are common to several signatures, and can therefore provide, in and of themselves, information on diagnosis, prognosis, treatment, etc. Specifics concerning signatures will be discussed in the corresponding sections below.

It should further be appreciated that the present invention is not limited to any particular disease, and that those skilled in the art will understand that the methods disclosed herein can be used to identify signatures for, and assess, other diseases, including those not specifically mentioned herein. The present invention is also not limited to use of mass spectrometry, or any particular type of mass spectrometry (e.g., electrospray ionization (ESI) tandom mass spectrometry (MS/MS), etc.), and includes other methods for quantifying metabolites, such as chromatography or spectrometry. That being said, the inventors have found that there are benefits to using mass spectrometry, and in particular ESI MS/MS, and the data analysis described herein (e.g., log-transformation, ROC curves, etc.). As such, the methods described in detail herein are preferred embodiments, and should be treated as such.

Prior to discussing the inventions, including individual signatures, the methods used to identify the same, and assess various diseases, certain definitions of term or phrases used herein will first be provided.

Definitions

By employing the biomarkers (or specific sets thereof) and the methods according to the present invention it has become possible to assess a disease (e.g., ovarian cancer, colorectal cancer, etc.) with improved accuracy and reliability. It has surprisingly been achieved in the present invention to provide biomarkers or biomarker sets by measuring the amount and/or ratios of certain metabolites in samples, such as blood samples, of subjects that make it possible to screen and diagnose diseases (e.g., ovary cancer, etc.) in an improved manner and at an early stage of the disease.

In general, a biomarker is a valuable tool due to the possibility to distinguish two or more biological states from one another, working as an indicator of a normal biological process, a pathogenic process or as a reaction to a pharmaceutical intervention.

A metabolite is a low molecular compound (<1 kDa), smaller than most proteins, DNA and other macromolecules. Small changes in activity of proteins result in big changes in the biochemical reactions and their metabolites (=metabolic biomarker, looking at the body's metabolism), whose concentrations, fluxes and transport mechanisms are sensitive to diseases and drug intervention.

This enables getting an individual profile of physiological and pathophysiological substances, reflecting both genetics and environmental factors like nutrition, physical activity, gut microbial and medication. Thus, a metabolic biomarker gives more comprehensive information than for example a protein or hormone, which are biomarkers, but not metabolic biomarkers.

In view thereof, the term "metabolic biomarker" or short "biomarker" as used herein is defined to be a compound suitable as an indicator of the presence and state of a disease (e.g., cancer) as well as its subtype (e.g., subtype of tumor), being a metabolite or metabolic compound occurring during metabolic processes in the mammalian body.

The terms "biomarker" and "metabolic biomarker" are in general used synonymously in the context of the present invention and typically refer to the amount of a metabolite or to the ratio of two or more metabolites. Hence, the term metabolic biomarker or biomarker is intended to also comprise ratios (or other mathematical relationships) between two or more metabolites.

The term "amount" typically refers to the concentration of a metabolite in a sample, such as blood sample, and is usually given in micromol/L, but may also be measured in other units typically used in the art, such as g/L, mg/dL, etc. The term "sum" typically means the sum of molar amount of all metabolites as specified in the respective embodiment.

The term "ratio" typically means the ratio of amounts of metabolites as specified in the respective embodiment. The metabolic biomarker (set) measured according to the present invention may comprise the classes of metabolites (i.e. analytes) of amino acids and biogenic amines, acylcarnitines, hexoses, sphingolipids and glycerophospholipids, as listed in FIGS. 2-6.

Biogenic amines in FIG. 2 are understood as a group of naturally occurring biologically active compounds derived by enzymatic decarboxylation of the natural amino acids. A biogenic substance is a substance provided by life processes, and the biogenic amines contain an amine group.

It has surprisingly been found that measuring a set of biomarkers comprising these classes of metabolites, i.e. measuring the amount and/or ratios of certain indicative metabolites, allows for screening and diagnosing various diseases (e.g., ovary cancer, etc.) in an improved manner and at an early stage and allows for assessing biochemical reflection of tumor activity, allowing for the prediction of a therapeutic response as well as for sub classification among a disease's behavior.

While a modified "signature" can be used, if one metabolite or one class of metabolites as specified for the respective biomarker combination is omitted or if the number thereof is decreased the assessment of the disease becomes less sensitive and less reliable.

This particularly applies for the early stages of the disease being not reliably detectable according to known methods using known biomarkers at all. In fact, the measurement of the metabolites contained in the respective sets of biomarkers at the same time allows a more accurate and more reliable assessment of a disease, typically with (A) a sensitivity of greater than 80%, preferably greater than 90%, and more preferably greater than 98%, (B) a specificity of greater than 80%, preferably greater than 85%, and more preferably greater than 90%, (C) a positive predictive value (PPV) of greater than 40%, preferably greater than 50%, and more preferably greater than 60%, and (D) a negative predictive value (NPV) of greater than 80%, preferably greater than 90%, and more preferably greater than 98%. Obviously, biomarkers (or sets thereof) that can reach or achieve 100% (or near 100%) sensitivity, specificity, PPV, and/or NPV is desired.

The meanings of the terms "sensitivity", "specificity", "positive predictive value" and "negative predictive value" are typically known in the art and are defined in the context of the present invention according to the "Predictive Value Theory", as established by the University of Iowa, USA. In this theory, the diagnostic value of a procedure is defined by its sensitivity, specificity, predictive value and efficiency. Description of the formulae are summarized below.

Sensitivity of a test is the percentage of all patients with disease present who have a positive test. $(TP/(TP+FN))\times 100$=Sensitivity (%) where TP=Test Positive; FN=False Negative.

Specificity of a test is the percentage of all patients without disease who have a negative test. (TN/(FP+TN))×100=Specificity (%) where TN=Test Negative; FP=False Positive.

Predictive value of a test is a measure (%) of the times that the value (positive or negative) is the true value, i.e. the percent of all positive tests that are true positives is the Positive Predictive Value ((TP/(TP+FP))×100=Predictive Value of a Positive Result (%); ((TN/(FN+TN))×100=Predictive Value Negative Result (%))

Likelihood Ratios: The performance of biomarkers can further be assessed by determining the Positive and Negative Likelihood Ratios (LR) used herein during Statistical Univariate Analysis (see FIG. 10).

Multivariate Data Analysis: Training cases were used for marker discovery and to identify any clinical variable that might be associated with a disease (e.g., ovarian cancer, colorectal cancer, etc.) by logistic regression analysis. Quantification of metabolite concentrations and quality control assessment was performed with the MetIDQ® software package (BIOCRATES Life Sciences AG, Innsbruck, Austria). Internal standards serve as the reference for the metabolite concentration calculations. An xls file was then exported, which contained sample names, metabolite names and metabolite concentration with the unit of μmol/L of in plasma.

Data was then uploaded into the web-based analytical pipeline MetaboAnalyst 2.0 (www.metaboanalyst.ca) and normalized using MetaboAnalyst's normalization protocols (Xia et al 2012) for uni and multivariate analysis, high dimensional feature selection, clustering and supervised classification, functional enrichment as well as metabolic pathway analysis.

Data was also imported to ROCCET (ROC Curve Explorer & Tester) available at http://www.roccet.ca/ROCCET/ for the generation of uni and multivariate Receiver Operating Characteristic (ROC) curves obtained through Support Vector Machine (SVM), Partial Least Squares-Discriminant Analysis (PLS-DA) and Random Forests.

Curves were generated by Monte-Carlo cross validation (MCCV) using balanced subsampling where two thirds (⅔) of the samples were used to evaluate the feature importance. Significant features were then used to build classification models, which were validated on the ⅓ of the samples that were left out. The same procedure was repeated multiple times to calculate the performance and confidence interval of each model.

Up and down regulation: An up-regulation means an increase in the concentration of a metabolite, e.g. an increase in the rate of at which this biochemical reaction occurs due to for example a change in enzymatic activity. For a down-regulation, it's the other way around.

T-test: The t-test is a statistical hypothesis test and the one used is the one integrated in the MarkerView software and is applied to every variable in the table and determines if the mean for each group is significantly different given the standard deviation and the number of samples, e.g. to find out if there is a real difference between the means (averages) of two different groups.

P-value: The p-value is the probability of obtaining a result at least as extreme as the one that was actually observed, assuming that the null hypothesis (the hypothesis of no change or effect) is true. The p-value is always positive and the smaller the value the lower the probability that it is a change occurrence. A p-value of 0.05 or less rejects the null hypothesis at the 5% level, which means that only 5% of the time the change is a chance occurrence. This is the level set in the tables provided herein.

Log-fold change: Log-fold change is defined as the difference between the average log transformed concentrations in each condition. This is a way of describing how much higher or lower the value is in one group compared to another. For example, a log-fold change of 0.3 is "equivalent" to an exp (0.3)=1.34 fold change increase compared to the control (healthier group). Further, a log-fold change of −0.3 is "equivalent" to a exp(−0.3)=0.74=(1/1.34) fold change increase compared to the control or decrease fold change of 1.34 to the disease. See FIG. 11 for ideal tumor marker according to Sokoll and Chan.

Signatures for particular diseases, including the identification thereof and use of the same for assessing (e.g., screening, diagnosing, prognosing, treating, etc.) particular diseases, will now be discussed.

Breast Cancer—Patients and Methodology

Studies were first performed to identified signatures that could be used to assess breast cancer. In total 1113 baseline samples were used, 935 being from blood and 170 being from tissue samples. The samples were analyzed by the same, standardized, targeted quantitative mass spectrometry technique at the same centralized and independent fee-for-service company (Biocrates, Austria).

The cancer groups (n=447) were composed by i) breast cancer volunteers (n=217) comprising pT1pN0 (n=68), pT1N1 (n=77), pT2N1 (n=8), T2N0M0 (n=1) and T3N2M0 (n=63)]. Intrinsic subtypes were: i-luminals A (n=33), B (n=98), B-HER2 (n=23), triple negatives (n=37), HER-2 (n=14) and RE-/PR- (n=4). European patients (n=154) were composed by a retrospective (n=62) and a prospective arm (n=92) in addition to ii) lung (n=23), iii) head and neck (n=56), iv) liver (n=30), v) hematological malignancies (n=65) and vi) colon cancer patients (n=85) together to respective normal (n=85) and tumor tissues (n=85). Colon cancer patients were T1N0M0 (n=9), T2N0M0 (n=15), T3N0M0 (n=20), T3N0M1 (n=1), T3N1M0 (n=10), T3N1M1 (n=6), T3N2M0 (n=6), T3N2M1 (n=7), T4N0M0 (n=2), T4N1M0 (n=1), T4N1M1 (n=3), T4N2M0 (n=2), T4N2M1 (n=3).

The remaining 666 samples were included as control groups, out of which: 169 controls (79 women and 90 men) were from the São Paulo Population-based Health Investigation Project (ISA 2008), high risk of breast cancer development at baseline (n=48) and 1 year later (n=27), histologically proven non-invasive in situ carcinoma (n=21), low risk of breast cancer development (n=31) were defined as women with complete normality from mammographic (BI-RADS 1) as well as ultrasound perspectives and additionally scoring lower Gail Index values (<1.67), polycystic ovary syndrome (n=49), HIV-infected individuals prior of treatment (n=18), hemolytic disorders-paroxysmal nocturnal hemoglobinuria (n=31) and autoimmune hemolytic anemia (n=27), cirrhosis (n=30), hyper (n=8) and hypo thyroid (n=8) function and engraftment day of patients submitted stem cell allogeneic transplant (n=29).

Breast cancer patients with locally regional advanced tumors T3N2M0 (n=63), were scheduled to receive a neo-adjuvant chemotherapy approach comprised of 4 cycles of doxorubicin (60 mg/m2) and cyclophosphamide (600 mg/m2), followed by 4 cycles of paclitaxel (175 mg/m2) conducted at the Barretos Cancer Hospital.

This part of the study was designed to have as an endpoint the identification of predictive signatures of tumor response in patients with stage III disease, during the accomplishment of the project "Neoadjuvant Chemotherapy in Locally Advanced Breast Cancer (LABC)" (clinical trials NCT00820690). Patients had a baseline assessment within 2 weeks before starting chemotherapy, hematological and non-hematological toxicities were recorded through complete blood counts, liver and kidney function as well as clinical evaluations at each cycle (one every 3 weeks and one month after the end of treatment.

Baseline tumor dimensions were calculated using clinical and radiological measurements and compared to the final tumor diameter that was recorded directly on the surgery product by a dedicated pathologist. Complete Pathologic Response (pCR) was defined as no histopathology evidence of any residual invasive and/or non-invasive disease in breast or nodes (ypT0/ypN0).

The same procedure was adopted to evaluate the metabolic signatures identified herein to different benign conditions in order to test how specific and peculiar they were to breast cancer. To do so, comparisons were assembled among breast cancer women to the following cancer-free groups: A) Women at low risk of breast cancer development (n=31), B) Population-based controls (79 women and 90 men), C) Autoimmune disease (n=27), D) High risk of breast cancer development (n=36), E) Polycystic ovary syndrome (n=49), F) HIV-infected individuals prior of any treatment (n=18), G) Chemically-induced immune suppression of patients on the engrafting day after bone marrow heterologous stem cell transplantation (n=26).

In order to test whether metabolic deviations detected in stage III breast cancer women could play any role in disease-free survival, the initial findings were challenged against an earlier stage study the "Risk Prediction of Breast Cancer Metastasis Study" (Italy and Austria). The study was designed to have as an endpoint the identification of metabolic signatures of five years survival outcomes and included a total of 154 cases classified as luminal (75.3%, 116/154) and non-luminal (24.6%, 38/154) during a prospective (n=92) and retrospective (n=62) arms of women comprising pT1pN0 (n=68), pT1N1 (n=77), pT2N1 (n=8), T2N0M0 (n=1).

Comparison of breast cancer metabolomics to population-based controls was conducted to further explore the hypothesis that the initial results could be related to inborn errors of metabolism. Therefore, comparison was conducted against 169 age-matched men and women, with available blood samples at baseline, of the São Paulo Population-based Health Investigation Project (ISA 2008) designed to prospectively analyze the use of public health service in the city of São Paulo, SP, Brazil.

In order to identify any metabolic resemblances between breast cancer signatures and women at elevated risks of breast cancer development, our findings were challenged against a group of 41 women exhibiting relative risks ranging from 1.2 to 2.0 in addition to a group of PCOS women depicting HOMA-IR>2.5 (n=8) and <2.5 (n=10).

Participants completed a health history questionnaire, including information on race, age at menarche, age at first live birth, number of biopsies, presence of atypical hyperplasia, and family history of breast and ovarian cancer. Using the Breast Cancer Risk Assessment Tool (BCRAT), the 5-year absolute and relative risks (RRs) of breast cancer were estimated using source code version 3.0 from the National Cancer Institute website.

To explore the possibility of breast cancer being followed by energy metabolism deficiencies, the Lac/Pyr molar ratio was applied to the 154 European breast cancer patients adopting cutoff values >25 to suggest patients as harboring a primary (or secondary) respiratory chain dysfunction. To do so, besides quantification of 186 metabolites quantified in all participants, there was additional quantification (mmol/L) of the following metabolites in blood of the 154 European breast cancer participants: lactate, pyruvate-oxaloacetate, succinate, fumarate and alphaketoglutarate by using the same mass spectrometry approach adopted to the other measurements.

To gain accesses on how closer to metabolic stemness our results could be, our findings were compared to human embryo culture media used during assisted reproduction procedures. Culture was performed following routine protocols (Borges et al 2015) adopted for intracytoplasmic sperm injection (ICSI) procedures in the Reproduction Section at the Federal University of São Paulo, Brazil. After uterine transfer of embryos, the remaining embryo-free media were immediately frozen and kept at −80° C. until be analyzed by the same targeted quantitative MS/MS approach. Samples were divided into groups based on their degree of expansion and hatching status on day 3. Thus, two pooled groups comprising culture media of embryos of poor (n=100) and good development (n=100) were assembled and submitted to mass spectrometry analysis.

To further confirm the theory as well as to validate ratios as proxies for enzyme activity related to insulin-dependent MYC activation, mice obtained from the Centro de Desenvolvimento de Modelos Experimentais para Medicina e Biologia (CEDEME) of the Universidade Federal de São Paulo were maintained at a 12-hr light-dark cycle with ad libitum access to tap water and chow diet. Dietary calories restriction was performed according to the protocol of the National Institute on Aging. Briefly, 12-week old mice were divided in two groups: the ad libitum group, which had free access to the NIH31 diet (Harlan-Teklab) throughout the whole protocol, or the dietary restriction group, which was fed the NIH31/NIA Fortified (Harlan-Teklab) starting with a 10% decrease in caloric intake for a week, increased to 25% restriction in the following week, and to 40% restriction until the end of the protocol. Food intake and body weight were assessed weekly. Protocols for animal use were approved by the IACUC of the Universidade Federal de São Paulo (CEP-0218/11, CEP-0237/12 and CEUA4603261015) and were in accordance with NIH guidelines.

Absolute quantification (μmol/L) of blood metabolites was achieved by targeted quantitative profiling of 186 annotated metabolites by electrospray ionization (ESI) tandem mass spectrometry (MS/MS) in 302 plasma samples, blinded to any phenotype information, on a centralized, independent, fee-for-service basis at the quantitative metabolomics platform from BIOCRATES Life Sciences AG, Innsbruck, Austria.

The experimental metabolomics measurement technique which included a targeted profiling scheme was used to quantitatively screen for fully annotated metabolites using multiple reaction monitoring, neutral loss and precursor ion scans. Quantification of metabolite concentrations and quality control assessment was performed with the MetIQ software package (BIOCRATES Life Sciences AG, Innsbruck, Austria) in conformance with 21 CFR Part 11, which implies proof of reproducibility within a given error range. An xls file was then generated, which contained sample identification and 186 metabolite names and concentrations with the unit of μmol/L of plasma.

For metabolomic data analysis, log-transformation was applied to all quantified metabolites to normalize the concentration distributions and uploaded into the web-based analytical pipelines MetaboAnalyst 3.0 (www.metaboanalyst.ca) and Receiver Operating Characteristic Curve Explorer & Tester (ROCCET) available at http://www.roccet.ca/ROCCET (Xia et al 2013) for the generation of uni and multivariate Receiver Operating Characteristic (ROC) curves obtained through Support Vector Machine (SVM), Partial Least Squares-Discriminant Analysis (PLS-DA) and Random Forests as well as Logistic Regression Models to calculate Odds Ratios of specific metabolites.

ROC curves were generated by Monte-Carlo Cross Validation (MCCV) using balanced sub-sampling where two thirds (⅔) of the samples were used to evaluate the feature importance. Significant features were then used to build classification models, which were validated on the ⅓ of the samples that were left out on the first analysis. The same procedure was repeated 10-100 times to calculate the performance and confidence interval of each model.

To further validate the statistical significance of each model, ROC calculations included bootstrap 95% confidence intervals for the desired model specificity as well as accuracy after 1000 permutations and false discovery rates (FDR) calculation.

In total, 186 annotated metabolites were quantified using the p180 kit (BIOCRATES Life Sciences AG, Innsbruck, Austria), being 40 acylcanitines (ACs), 21 amino acids (AAs), 19 biogenic amines (BA), sum of hexoses (Hex), 76 phosphatidylcholines (PCs), 14 lyso-phosphatidylcholines (LPCs) and 15 sphingomyelins (SMs). glycerophospholipids were further differentiated with respect to the presence of ester (a) and ether (e) bonds in the glycerol moiety, where two letters denote that two glycerol positions are bound to a fatty acid residue (aa=diacyl, ae=acyl-alkyl), while a single letter indicates the presence of a single fatty acid residue (a=acyl or e=alkyl). In the same company (Biocrates), the European participants had their samples additionally analyzed for the following energy metabolism metabolites: lactate, pyruvate/oxaloacetate, alpha ketoglutarate, fumarate and succinate.

In addition to individual quantification, groups of metabolites related to specific functions were analyzed. Groups of AAs were computed by summing the levels of AA belonging to certain families or chemical structures depending on their functions such as the sum of: 1) essential amino acids (Essential AA), 2) non-essential amino acids (non-Essential AA), 3) glucogenic (Ala+Gly+Ser) amino acids (Gluc AA), 4) branched-chain (Leu+Ile+Val) amino acids (BCAA), 5) Aromatic (His+Tyr+Trp+Phe) amino acids (Arom AA), 6) Glutaminolytic derivatives (Ala+Asp+Glu), and 7) the sum of total amino acids.

Groups of acylcarnitines (AC), important to evaluate mitochondrial function, were also computed by summing Total AC, C2+C3, C16+C18, C16+C18:1 and C16-OH+C18:1-OH). Groups of lipids, important to evaluate lipid metabolism, were also analyzed by summing: 1) Total lysophosphatidylcholines (total LPC), 2) Total acyl-acyl and 3) Total acyl-alkyl phosphatidylcholines (total PC aa and total PC ae, respectively), 4) Total sphingomielins (total SM) and 5) Sum of total (LPC+PC aa+PC ae+SM) lipids (Structural lipids).

Proportions among sums of saturated, monounsaturated and polyunsaturated structural lipids were also assembled as proxies to quantify elongases and desaturases activities towards ether lipids: 1) Desaturase 9 [(PC ae C36:1+PC ae C38:1+PC ae C42:1)/(PC ae C42:0)], Desaturase 6 [(PC ae C44:6+PC ae C44:5+PC ae C42:5+PC ae C40:6+PC ae C40:5+PC ae C38:6+PC ae C38:5+PC ae C36:5)/(PC ae C36:1+PC ae C38:1+PC ae C42:1)].

Clinical indicators of liver metabolism and function were obtained by the applying either the classical (leucine+isoleucine+valine)/(tyrosine+phenylalanine) or variations (Val/Phe, Xleu/Phe) of the Fischer's quotient. Clinical indicators of isovaleric acidemia, tyrosinemia, urea cycle deficiency and disorders of β-oxidation were calculated by adopting the ratios of valerylcarnitine to butyrylcarnitine (C5/C4), tyrosine to serine (Tyr/Ser), glycine to alanine and glutamine (Gly/Ala, Gly/Gln) and lactate to pyruvate (Lac/Pyr), respectively.

Proxies for enzyme function related to the diagnosis of very long-chain acyl-CoA dehydrogenase (VLCAD) and type two carnitine-palmitoyl transferase (CPT-2) deficiencies were achieved by assembling the ratios (C16+C18:1/C2), (C14:1/C4), (C14:1-OH/C9), (C14/C9), (C14:1/C9) and to the elongation of very-long-chain-fatty acids (ELOVL2) (PC aa C40:3/PC aa C42:5). Levels of methionine sulphoxide (Met-SO) alone or in combination to unmodified methionine (Met-SO/Met) as well as symmetric (SDMA), asymmetric (ADMA) and total dimethylation of argine residues (Total DMA) were quantified to gain access to ROS-mediated protein modifications as well as to systemic arginine methylation status, respectively.

To gain access to MYC activity in blood, specific quantification of metabolites and ratios resulting from MYC-responsive enzymes activities were performed in the blood of hypoglycemic mice before and after insulin administration as well as in cancer-free women depicting normal (<2.5) and elevated (>2.5) HOMA (IR) values. Knowing that liver inhibition of gluconeogenesis is a bona fide insulin-MYC-dependent biochemical reaction, a shift from normal to lower values in the ratio of glucose to glucogenic amino acids (Glucose/Ser, Glucose/Gly and Glucose/Ala) after insulin administration as well as in women with elevated HOMA (IR) values, was adopted as a measurement of insulin-MYC-related activity.

The same procedure was then applied to other MYC-responsive enzymes as follows: arginine methyltransferases (ADMA, ADMA/Arg, SDMA, SDMA/Arg and Total DMA, Total DMA/Arg), ornithine decarboxylase (Glu, Glu/Orn, Pro, Pro/Orn, Orn, Orn/Arg, Putrescine, Putrescine/Orn, Spermidine, Spermidine/Putrescine, Spermine and Spermine/Spermidine), alanine am inotransferase (Ala), (Ala/Glu), aspartate aminotransferase (Asp) and (Asp/Glu), glutaminase (Glu), (Gln/Glu), [(Glu+Asp+Ala)/Gln], [(Gln/Glu)/Asp], (Glu/Glucose)/(Ala/Glu) and [(Glu/Gln)/Glucose]/(Ala/Glu).

The later 2 ratios were specifically assembled based on in vitro experiments related to the "glutamate pulling effect" which is defined as the hypoglycemia-induced up-regulation in the deaminated, rather than transaminated, production of glutamate through insulin-MYC-dependent glutamate dehydrogenase (GDH) stimulation of glutaminolysis with consequent increased amounts of net keto acids to anaplerosis. Because lower microenvironmental pH values are also reported to favor the "glutamate pulling effect" we also calculated the degree of correlation between increases in lactate and glutamate by Pearson r correlation analysis.

The ratios of serine to C2 (Ser/C2) and of (PC aa C42:0/PC ae C32:3) were additionally included as proxies for glycolysis-related phosphoglycerate dehydrogenase (PHGDH) and glucokinase regulator (GCKR) activities. The later inhibits glucokinase activity in liver and pancreas and the former catalyses the rate limiting step of serine biosynthesis. In parallel, and assuming the ratio values of glutamine to glutamate (Gln/Glu) and to aspartate [(Gln/Glu)/Asp], as proxys for glutaminolytic activity, the inventors assembled the ratios [(Ser/C2)/(Gln/Glu)], [(Ser/C2)/(Gln/Glu)/Asp], [(PC aa C32:2/PC ae C34:2)/(Gln/Glu)] and [(PC aa C32:2/PC ae C34:2)/(Gln/Glu)/Asp] as theoretical equations to gain access to the balance between glycolysis and glutaminolysis.

Other Diseases—Patients and Methodology

In light of the foregoing, studies were then performed to identified signatures (i.e., other signatures) that could be used to assess other diseases, such as ovarian cancer, colorectal cancer, pancreatic cancer, and acute graft-versus-host disease, to name a few.

In certain embodiments, the disease at issue is cancer (e.g., ovarian cancer, etc.), and may be at a particular stage (e.g., stages I, II, III or IV). Definition of the medical stages of cancer is defined by the American Joint Committee on Cancer (AJCC) of the United States National Cancer Institute at the National Institutes of Health. The staging system provides a strategy for grouping patients with respect to prognosis. Therapeutic decisions are formulated in part according to staging categories but primarily according to tumor size, lymph node and distant metastasis status.

Regardless of the disease at issue, the biological sample is obtained from a mammal, preferably from a mouse, a rat, a guinea pig, a dog, a mini-pig, or a human, most preferably human, further preferably from a woman. The biological sample preferably is blood, however, any other biological sample known to the skilled person, which allows the measurements according to the present invention is also suitable. The blood sample typically is full blood, serum or plasma, wherein blood plasma is preferred. Dried samples collected in paper filter are also accepted. Thus, the methods according to the invention typically are in vitro methods.

For the measurement of the metabolite concentrations in the biological sample a quantitative analytical method such as chromatography, spectroscopy, or mass spectrometry is employed, where chromatography may comprise GC, LC, HPLC, and UPLC, spectroscopy may comprise UV/Vis, IR, and NMR, and mass analyzers/spectrometry may comprise ESI-QqQ, ESI-QqTOF, MAL¬DI-QqTOF, and MAL¬DI-TOF-TOF. More preferably, mass analyzers/spectrometry comprises Quadrupole Mass Analyzers, Ion Trap Mass Analyzers, TOF (Time of Flight) Mass Analyzer, Orbitrap mass analyser, Magnetic Sector Mass Analyzer, Electrostatic Sector Mass Analyzer, Ion Cyclotron Resonance (ICR) and combinations of mass analyzers, including single quadrupole (Q) and triple quadrupole (QqQ), QqTOF, TOF-TOF, Q-Orbitrap. The inventors have discovered that use of FIA- and HPLC-tandem mass spectrometry is preferred and has certain benefits.

Abbreviations that are used herein are as follows: GC=Gas Chromatography, CE=Capillary electrophoresis, LC=Liquid Chromatography, HPLC=High Pressure Liquid Chromatography, UHPLC=Ultra High Pressure Liquid Chromatography, UV-Vis=Ultraviolet-Visible, IR=Infrared, NIR=Near Infrared, NMR=Nuclear Magnetic Ressonance, ESI=Electron Spray Ionization, MALDI=Matrix-assisted laser desorption/ionization, TOF=Time-of-Flight, APCI=Atmospheric pressure chemical ionization, QqQ=Triple quadrupole configuration also known as Q1q2Q3 (Q1 and Q3 quadrupoles are mass filters and q2 is a no mass-resolving quadrupole).

For measuring the metabolite amounts targeted metabolomics is used to quantify the metabolites in the biological sample including the analyte classes of amino acids, biogenic amines, acylcarnitines, hexoses, sphingolipids and glycerophospholipids. The quantification is done using in the presence of isotopically labeled internal standards and determined by the methods as described above. A list of analytes including their abbreviations (BC codes) being suitable as metabolites to be named according to the invention is indicated in FIGS. 2-6.

In order to reach the highest capability to detect a disease using metabolomics, the present invention identified its discriminant biochemical features and ratios not only by comparing sick patients (i.e., ones having a particular disease, such as ovarian cancer) to healthy controls but also to a larger group of participants with other malignant and benign conditions. Samples were prospectively collected and analyzed by the same, fee-for-service, standardized, targeted quantitative mass spectrometry technique at the same centralized and independent company (Biocrates, Austria).

A group of plasma samples of woman having certain cancers at various stages (i.e., stage I, II and III) with no previous treatment were included, the cancer patients (n=473) were composed by: i) breast cancer volunteers from Brazil and Europe (n=213) in addition to ii) lung (n=23), iii) head and neck (n=56), iv) liver (n=30), v) hematological malignancies (n=65), and vi) colon cancer patients (n=85) together to respective normal (n=85) and tumor tissues (n=85).

The remaining 752 samples were included as control groups, out of which: 169 controls (79 women and 90 men) were from the São Paulo Population-based Health Investigation Project (ISA 2008) that due to its population characteristics, allowed us to analyzed them according their frequency of metabolic syndrome distributed according the 6 progressive stages following the recommendation of the Joint Interim Statement of the International Diabetes Federation Task Force on Epidemiology and Prevention; National Heart, Lung, and Blood Institute; American Heart Association; World Heart Federation; International Atherosclerosis Society; and International Association for the Study of Obesity.

Controls also included 33 women at elevated risks of breast cancer development, 23 participants with histologically proven non-invasive in situ carcinoma, 31 women at low risk of breast cancer development, 49 with polycystic ovary syndrome, 18 HIV-infected individuals prior of treatment, 34 women with rheumatoid arthritis, 58 autoimmune hemolytic disorders, 30 participants with cirrhosis, 8 with hyper and 8 with hypothyroidism.

Targeted (ESI-MS/MS) Quantitative Metabolomics/Lipidomics profiling, was performed in an independent validation set with plasma samples from woman with various cancers as well as a number of controls, on two independent, fee-for-service basis using quantitative metabolomics platform at Biocrates Life Sciences AG, Innsbruck, Austria and Quest Diagnostics Nichols Institute San Juan Capistrano, Calif., USA.

Briefly, a targeted profiling scheme was used to quantitatively screen for known small molecule metabolites using multiple reaction monitoring, neutral loss and precursor ion scans. Quantification of the metabolites of the biological sample is achieved by reference to appropriate internal standards and the method has been proven to be in conformance with 21 C.F.R., Part 11, which implies proof of reproducibility within a given error range. Concentrations of all analyzed metabolites were reported in μM.

In total, 186 different metabolites were been detected being 40 acylcanitines, 19 proteinogenic aminoacids, ornithine and citrulline, 19 biogenic amines, sum of Hexoses, 76 phosphatidylcholines, 14 lyso-phosphatidylcholines and 15 sphingomyelins. See FIGS. 2-6.

Glycerophospholipids are further differentiated with respect to the presence of ester (a) and ether (e) bonds in the glycerol moiety, where two letters (aa=diacyl, ae=acyl-alkyl, ee=dialkyl) denote that two glycerol positions are bound to a fatty acid residue, while a single letter (a=acyl or e=alkyl) indicates the presence of a single fatty acid residue.

Lipid side chain composition is abbreviated as Cx:y, where x denotes the number of carbons in the side chain and y the number of double bonds, e.g. "PC ae C38:1" denotes a plasmalogen/plasmenogen phosphatidylcholine with 38 carbons in the two fatty acid side chains and a single double bond in one of them.

Training cases were used for marker discovery and to identify any clinical variable that might be associated with a particular disease by logistic regression analysis. Quantification of metabolite concentrations and quality control assessment was performed with the MetIDQ® software package (BIOCRATES Life Sciences AG, Innsbruck, Austria). Internal standards serve as the reference for the metabolite concentration calculations. An xls file was then exported, which contained sample names, metabolite names and metabolite concentration with the unit of μmol/L of in plasma.

Data was then uploaded into the web-based analytical pipeline MetaboAnalyst 2.0 (www.metaboanalyst.ca) and normalized using MetaboAnalyst's normalization protocols (Xia et al 2012) for uni and multivariate analysis (see above discussion concerning normalization), high dimensional feature selection, clustering and supervised classification, functional enrichment as well as metabolic pathway analysis.

Data was also imported to ROCCET (ROC Curve Explorer & Tester) available at http://www.roccet.ca/ROCCET/ for the generation of uni and multivariate Receiver Operating Characteristic (ROC) curves obtained through Support Vector Machine (SVM), Partial Least Squares-Discriminant Analysis (PLS-DA) and Random Forests.

Curves were generated by Monte-Carlo cross validation (MCCV) using balanced subsampling where two thirds (⅔) of the samples were used to evaluate the feature importance. Significant features were then used to build classification models, which were validated on the ⅓ of the samples that were left out. The same procedure was repeated multiple times to calculate the performance and confidence interval of each model.

Breast Cancer Signature

Breast cancer remains a leading cause of morbidity and mortality throughout the world. Earlier diagnosis through the application of mammography and magnetic resonance imaging has improved the detection of smaller volume disease providing physicians the opportunity to intervene at earlier stages when the cancers are most curable.

The advent of molecular technologies, widely applied in prognostic determinations, have evolved into diagnostic tools that utilize circulating tumors cells and cell free DNA for earlier detection, prognosis and where applicable response prediction. Numerous clinical trials are now exploring the clinical utility of these approaches.

Research shows that human cancers evolve in an environment of metabolic stress. Rapidly proliferating tumor cells deprived of adequate oxygen, nutrients, hormones and growth factors up-regulate pathways that address these deficiencies to overcome hypoxia (HIF), vascular insufficiency (VEGF), growth factor deprivation (EGFR, HER2) and the loss of hormonal support (ER, PR, AR) all to enhance survival and proliferation.

Many oncogenes are now known to regulate metabolic pathways that are critical for cell survival in the inhospitable tumor micro-environment, where oxygen and nutrient sources are highly limited. Indeed RAS, PI3K, TP53 and MYC among others are now recognized to be important metabolic regulators whose functions are fundamental for tumor cell survival.

Based upon the growing recognition that cancer cells differ from their normal counterparts in their use of nutrients, synthesis of biomolecules and generation of energy, we applied quantitative mass spectrometry to the blood and tissue of patients with breast cancer and compared the results with those observed in normal controls. To explore commonalties, the inventors extended these studies to include other cancers of glandular and non-glandular ancestries and to non-malignant disease states associated with metabolic stress including poly cystic ovary syndrome and advanced metabolic syndrome.

The findings led to a murine model of insulin/glucose mediation of metabolic stress and finally to an exploration of the secretome of human embryos prior to implantation to examine the "stemness" of the signals observed.

To evaluate the possible differences and likenesses among breast cancer and tumors of distinctive histology and locations, the identified blood signatures were compared to blood samples from treatment-naive lung (n=23), plasma from prostate cancer patients (n=10), head and neck (n=57), liver (n=30) and colon cancer patients (n=85), the latter with respective normal (n=85) and tumor tissues (n=85) as well as hematological malignancies (n=36). Normal (n=85) and tumor tissues (n=85) from patients harboring colon cancer, were also used to validate, at tissue level, the metabolic communalities identified in blood and shared by breast and colon cancer.

Important, each individual type of cancer, besides comparison to different malignancies, were also compared to the group of 666 controls described above containing 12 different benign metabolic conditions. After multivariate ROC curve analysis, the ratios shown in FIGS. 7A and B emerged as the representation of the metabolic scenario depicting the highest specificity to each individual tumor.

The search for metabolic intermediates, the blood concentrations of which (μM/L) could be utilized as breast cancer biomarkers led to the assembly of an exploratory data set that compared plasma samples from women at low risk of breast cancer (n=31) with plasma samples from patients with treatment-naive stage III (T3N2M0) invasive disease (n=59). Targeted quantitative MS/MS analysis (1) coupled with unsupervised clustering analysis (online methods) identified clear metabolic differences between cases and controls (FIG. 1a). Validation was then undertaken (statistical power=0.8) that compared 169 population-based control samples, against results obtained in 154 cases from an independent and earlier reported disease cohort the "Risk Prediction of Breast Cancer Metastasis Study" (Italy and Austria).

Results demonstrated that breast cancer women exhibited at least one up- or down-regulated metabolite from amongst the 5 principal classes of metabolites that were quantified in blood. Statistical analysis depicts the individual validation of nine of these metabolites, originally identified in the exploratory phase including glutamine (Gln), aspartate (Asp), glutamate (Glu), lysophosphatidylcholine acyl C26:1 (lysoPC a C26:1), Sphingomyelin C18:0 (SM C18:0), 3-Hydroxytetradecenoylcarnitine (C14:1-OH), phosphatidylcholine acyl-alkyl C38:3 (PC ae C38:3), methionine sulfoxide (Met-SO) and taurine.

Among the observations in both, the exploratory and the validation sets, was the finding that glutamine concentrations in the cancer patients were reduced to nearly ⅛ of the levels observed in the normal population (~800 μM/L) (p=7.8e-53, FDR=2.7e-52), while blood concentrations of aspartate (p=1.7e-67, FDR=8.3e-67) (FIG. 1e) and glutamate (p=6.4e-96, FDR=6.2e-95) were nearly 10 fold higher than the normal ranges of 0-5 μM/L and 40 μM/L, respectively.

As glutamine consumption associated with parallel increases in glutamate and aspartate is considered a hallmark of MYC-driven "glutaminolysis," these findings led an examination of other MYC-associated phenomena to interrogate the observations.

Hepatic glutamine (Gin) metabolism regulates the level of amino acids in the circulation and Glutamate (GLU) through its role in numerous trans-deamination reactions is central to this process.

As MYC activation is associated with measurable changes in blood levels of specific metabolites including glutamine, glutamate, the ratios thereof and others, targeted quantitative MS/MS was used to evaluate (μM/L) these intermediates as surrogate markers for MYC activation. The inventors then assembled metabolite ratios measured directly in blood to serve as "proxies" for MYC-coordinated metabolic functions.

In agreement with their hypothesis, the Gln/Glu ratio, a negative surrogate for glutamine metabolism, i) discriminated breast cancer cases from controls; ii) inversely correlated (Correlation=−0.54, p=3.67e-6 FDR=3.06e-5) with elevated breast cancer risk; iii) correlated with the risk of 5-year mortality in pathological stage I patients, and iv) inversely correlated with the failure to achieve pathologic complete remission (pCR) after neo-adjuvant chemotherapy (NAC) (Correlation=−0.81, p=1.15e-81, FDR=2.13e-80).

Parallel analyses found that the Gln/Glu ratio inversely correlates with i) late stage metabolic syndrome and with ii) increased chance of death in both the retrospective and prospective arms of the European cohort (Correlation=−0.68, p=2.30e-38, FDR=1.59e-37).

Theoretically, changes in glutamine consumption, reflected by the Gln/Glu ratio could provide a metabolic link between breast cancer initiation and diabetes, reflective of a systemic metabolic reprogramming from glucose to glutamine as the preferred source of precursors for biosynthetic reactions and cellular energy.

The inventors found the same changes in the Gln/Glu ratio in nearly 100% of breast cancer patients, independent of intrinsic subtype. These breast cancer patients revealed systemic MYC-associated biochemical shifts, previously described in vitro, associated with glutamine utilization over glucose for the synthesis of structural phospholipids, as measured by the ratios (Structural Lipids/Gln) and (Structural Lipids/Hexoses), respectively. The MYC signatures in breast cancer patients and their similarity to diabetes mellitus raised the question whether metabolic re-programming might be identified through the measurement of other biochemical intermediates.

To examine breast cancer against other disease states, the results were compared with those obtained from other cancers (30 liver; 23 lung; 85 colon; 58 head & neck and 65 hematologic) and from individuals with various metabolic conditions including late stages of metabolic syndrome (n=70), HCV-induced cirrhosis (n=30); hyperthyroidism (n=8); hypothyroidism (n=8); HIV infection (n=18); polycystic ovary syndrome (n=49); auto immune disease (n=86) and with those from women at elevated risk for breast cancer (n=33).

The inventors measured biochemically-active metabolites that had previously been described in large metabolomics and genome-wide association studies to examine established single metabolite and metabolite ratios related to: i) liver function (Val/Phe, Xle/Phe), ii) lipid desaturase activity (PC aa C36:6) and iii) serine palmitoyltransferase (SPTLC3) activity (PC aa C28:1 and C10:2). These measures were used to develop algorithms for the interrogation of the data sets.

Results, as multivariate Receiver Operator Curve (ROC) analyses, using the equation {[PC aa 36:6/[(Val/Phe)/Taurine]/C10:2} and the lipid PC aa C28:1, were found to segregate breast cancer from controls, irrespective of stage (I to III) and intrinsic subtypes, in both the exploratory [AUC=0.987 (95% CI: 0.964-1), sensitivity=96.72%, specificity=96.78%, positive predictive value=98.33%, negative predictive value=93.94%, average accuracy (100-fold cross validations)=0.95 and predictive accuracy statistics (1000 permutations)=p<2.04e-05] and validation sets [AUC=0.995 (95% CI: 0.991-0.998), sensitivity=98.09%, specificity=96.18%, positive predictive value=82.35%, negative predictive value=99.64%, average accuracy (100-fold cross validations)=0.96 and predictive accuracy statistics (1000 permutations)=p<1.28e-06].

To confirm these associations, Pearson's r correlations (www.metaboanalyst.ca) were conducted that compared the described ratio values with levels of the oncometabolites fumarate, succinate, lactate, glutamine and hexoses measured in the blood of our 154 European breast cancer patients. The highest positive correlations were found with lactate (p=1.42e-08, FDR=3.24e-07), lactate/pyruvate (p=7.96e-06, FDR=7.47e-05), fumarate/hexoses (p=0.0004, FDR=0.002), succinate/hexoses (p=0.0001, FDR=0.0007) and the glutaminolysis-related ratio (Ala+Asp+Glu/Gln) (p=0.0004, FDR=0.002). When the (Lac/Pyr) values were applied to the logistic regression equation log it(P)=log[P/(1−P)]=−12.24+1.80 Lac/Pyr, where P is Pr(y=1|x), elevations in this ratio were associated with an increased risk of 5-years death (Odds=6.08 [Pr (>|z|)=0.001]) when analyzing patients with primary tumors not bigger than 2.0 cm (n=103).

The highest negative correlations were observed for hexoses/lactate (p=5.88e-08, FDR=1.11e-06); hexoses (p=0.002, FDR=0.007); and the liver gluconeogenesis ratios (hexoses/PHGDH Act) (p=0.002, FDR=0.007); and (hexoses/Ala+Gly+Ser) (p=0.0014, FDR=0.005); [hexoses/(C14:1/C4)] (p=0.003, FDR=0.009); [hexoses/(C18:1/C8)] (p=9.94e-05, FDR=0.0006); (hexoses/CPTII) (p=0.0007, FDR=0.003); [hexoses/(C16/C3)] (p=0.001, FDR=0.004); (hexoses/AcylC-DC) (p=0.002, FDR=0.007).

When the metabolic profiles of patients with different tumors (lung, colon, liver, leukemias, lymphomas and squamous cells carcinoma of head and neck) were examined, the results again demonstrated enhanced glutamine consumption, particularly in patients harboring tumors of glandular ancestries.

Extending these studies to include patients with polycystic ovary syndrome (PCOS), cirrhosis, high-risk of breast cancer and stage 5 metabolic syndrome revealed that these cancer-free participants manifested glutaminolytic profiles that were very similar to those found in adenocarcinoma patients.

The ratio (Glu/Hexoses) was assembled by us following the in vitro demonstration of the "glutamate pulling effect" where glucose starvation in malignant cells culture leads to elevations in glutamate through a MYC-coordinated reaction.

This effect was clearly identified in the blood of patients harboring adenocarcinomas, those at higher risk of breast cancer and individuals with PCOS. Noteworthy, neither of the control groups composed of population-based normal controls or patients with non-glandular tumors (leukemias, lymphomas, multiple myelomas and squamous cell carcinomas) revealed marked changes in this ratio, particularly squamous cell carcinomas that revealed similar levels to controls.

Increases in the "glutamate pulling effect" have been described under conditions of metabolic stress induced by glucose deprivation. In agreement, the inventors found a significant (p=0.003, FDR=0.009) inverse correlation between patient blood hexoses concentrations and the values of their breast cancer equation {[PC aa 36:64(Val/Phe)/Taurine]/C10:2}.

In line with the premise that glandular cancers are promoted under conditions of relative hypoglycemia, measured as the "glutamate pulling effect," their results suggest that the isolated determination of blood glucose levels may not be as informative as the measurement of hexose levels in relation to other metabolic intermediates including: i) the mitochondrial carnitine palmitoyltransferase II (CPT-2) deficiency ratio (C16/C3), ii) the peroxisomal impairment biomarkers lysoPC a C26:0, lysoPC a C26:1 and lysoPC a C28:1, or iii) its relation to glutaminolysis [Phe/(Gln/Glu)/Asp]. Importantly, both CPT-2 and peroxisomal deficiencies, well known inborn errors of metabolism, are associated with hypoglycemia in afflicted patients.

If a state of relative hypoglycemia were to occur in breast cancer as the result of inborn-like errors of metabolism, then hyperinsulinemia associated with chronic hypoglycemia would constitute a powerful metabolic stressor capable of systemically up-regulating glycolysis and glutaminolysis, even in the absence of cancer.

To examine the hypoglycemia premise, the inventors developed an experimental murine model in which insulin was administered to mice under normo- and hypoglycemic conditions. In this murine model only the hypoglycemic mice that received insulin recapitulated the MYC-dependent shifts that had been observed in cancer patients, characterized by the insulin/MYC-dependent reactions of i) glutaminolysis (Gln/Glu), (Ala/Glu) and [(Gln/Glu)/Asp] as well as glycolysis (Ser/C2) and the combination of both (Ser/C2)/[(Gln/Glu)/Asp], ii) glutamate pulling effect (Glu/Hexoses), iii) arginine methyltransferase activity [Total DMA/[(Gln/Glu)/Asp] and [Tau/[(Gln/Glu)/Asp], iv) liver function [BCAA/(Phe+Tyr)], ornithine decarboxylase activity (Spermidine), v) liver gluconeogenesis [Hexoses/(Ala+Gly+Ser)] and vi) peroxisomal impairment (lysoPC a C26:0).

To confirm these findings in humans, we examined whether blood concentrations of hexoses correlated with peroxisome dysfunction, as represented by the elevation of specific lipids containing very long chain fatty acids (VLCFA). "Pearson r" correlations were conducted to compare women at low risk of cancer (n=31), to women at elevated relative risk (scoring 1.7 to 1.9) (n=14), women with non-invasive (in situ) carcinoma (n=23), women with polycystic ovary syndrome (n=49), and those with invasive breast cancer both luminal (n=118) and non-luminal (n=36).

Results, from the ratios of hexoses to lysoPC a C26:1 (Correl.=−0.73, p=3.41e-49, FDR=2.89e-48) and hexoses to lysoPC a C28:1 (Correl.=−0.60, p=9.88e-30 and FDR=6.29e-29) demonstrated a progressive negative correlation beginning with women at high risk and in situ carcinoma, to PCOS and finally achieving a nadir in the plasma of patients with invasive disease, irrespective of intrinsic subtype.

The results suggest that breast cancer could be preceded by systemic subclinical disturbances in glucose-insulin homeostasis characterized by mild, likely asymptomatic, IEM-like biochemical changes. The process would include variable periods of hyperinsulinemia with the consequent systemic MYC activation of glycolysis, glutaminolysis, structural lipidogenesis and further exacerbation of hypoglycemia, the result of MYC's known role as an inhibitor of liver gluconeogenesis.

Under normal conditions hypoglycemia results in the recruitment of fatty acids from storage pools. However, individuals who carry a primary inability to utilize fatty acids as an energy source, as seen in Fatty Acids Oxidation Defects (FAOD), would be prone to the accumulation of toxic oncometabolites as well as carnitine and fatty acid derivatives with increased ROS production and further mitochondrial disarrangement.

In this context, the metabolic dependencies of cancer characterized by excessive glycolysis, glutaminolysis and malignant lipidogenesis, previously considered a consequence of local tumor DNA aberration could, instead, represent a systemic biochemical aberration that predates and very likely promotes tumorigenesis.

Furthermore, these metabolic disturbances would be expected to remain extant after therapeutic interventions which is consistent with the recent observation that breast cancer relapse rates remain unaltered up to 24 years following initial treatments.

In support for our hypothesis and consistent with the definition of IEM, the inventors detected the accumulation of very long chain acylcarnitines such as C14:1-OH (p=0.0, FDR=0.0), C16 (p=0.0, FDR=0.0), C18 (p=0.0, FDR=0.0) and C18:1 (p=1.73e-322, FDR=1.16-321) and lipids containing VLCFA (lysoPC a C28:0) (p=1.14-e95, FDR=1.65e-95) in the blood of breast and colon cancer patients. Strikingly these same profiles were identified not only in the colon tumor tissues but also in the adjacent normal colonic mucosa removed at the time of surgery from these same colon cancer patients.

The metabolic changes they describe in breast cancer arise in concert with IEM-like changes in oxidative phosphorylation as detected by increased values of the ratio lactate/pyruvate characteristic of Ox/Phos deficiency. In the study, 76% ($7\%_2$) of the European breast cancer patients had lactate/pyruvate ratios values higher than the normal value of 25.8.

Recent reports have identified a four-fold higher frequency of cancer (including breast) in patients with energy metabolism disorders and IEMs are associated with elevated hexose/insulin disorders and gonadal and thyroid dysfunction that are themselves associated with high lactate/pyruvate ratios.

Defects in oxidative phosphorylation can occur as a result of primary fatty acid oxidation deficiencies (FAOD) as they are associated with the systemic mitochondrial accumulation of toxic fatty acid and carnitine derivative intermediates.

To determine whether excessive glutaminolysis and glycolysis, as quantified in the current study, reflect systemic rather than local events, to was hypothesized that the identified oncogenic disturbances should be present in the normal tissues, other than blood, of patients who harbor malignancies.

If true, then the biochemical profiles identified in these normal tissue biopsies should provide similar prognostic information with regard to response and survival to the data generated directly from tumor biopsy material.

Among the most powerful metabolic equations for MYC-activation is that which links the widely used MYC-driven desaturation marker ratio of SFA/MUFA to the MYC glutaminolysis-associated ratio of (Asp/Gln). The inventors prior experience in 213 breast cancer and 200 controls revealed that the metabolic deviation underscored by this equation [(SFA/MUFA)/(Asp/Gln)] is one of the most robust breast cancer discriminants (AUC=1.0, p=1.32e-127).

ANOVA and unsupervised clustering comparisons were assembled to compare the blood metabolic phenotypes from controls (n=200), breast cancer (n=213) and colon cancer patients (n=85) with signatures obtained from both normal colonic epithelium (n=85) and colon cancers removed surgically from the same 85 CRC patients.

These results demonstrate virtually identical biochemical phenotypes, revealed by this equation in the blood of breast and colon cancer patients that are quantitatively indistinguishable from the phenotypic deviations detected in the normal and colon tumor tissues. When compared with the control group (n=200), the results from blood or tissue (both normal mucosa and tumoral) of the cancer patients are so concordant as to represent virtually indistinguishable biological samples.

Interestingly, the biochemical disturbances found in the normal colonic mucosa reflected in the ratio {(Ser/C2)/[(Gln/Glu)/Asp]}, significantly (p=1.63e-33, FDR=2.21e-33) correlated with the risk of relapse at 5 years indistinguishable from the results obtained with the colon tumors from these patients. This ratio not only clearly distinguished breast cancers from controls as well as women at low and high risk of cancer but also distinguished i) women with shorter (2.1 years) vs. longer (5.1 year) relapse-free survival, and ii) women who achieved complete pathological response (pCR) vs. patients with residual disease after NAC (p=3.73e-108, FDR=2.31e-107) (i.e., prognosis).

Additional observations in the present study found that liver dysfunction shares many features with both IEM and cancer suggesting a role for hepatic dysfunction in carcinogenesis.

Lower values of Fischer's quotient [(Ile+Leu+Val)/(Tyr+Phe) and ALT activity (Ala/Glu), were found in cancer-free women with PCOS, those with elevated risks of cancer development and those with established glandular malignancies (liver, breast, colon, lung). These recurring biochemical deviations include transamination and gluconeogenesis frailties and the incapacity to properly metabolize branched chain (BCAA) and aromatic amino acids.

The metabolic shifts evidenced by lower values in Fischer's ratio were not detected in any metabolic syndrome participant reflecting an accumulation of BCAA in blood, mainly in later stage disease, wherein the Fischer's ratios were found to be higher. In adenocarcinoma patients the lower values of Fischer's ratio seem to reflect a deterioration of liver function resulting in a simultaneous diminution in BCAA and the accumulation of aromatic amino acids. Indeed, phenylalanine levels in breast cancer patients were found to be greater on average 89.3 µM/L (75 to 128 µM/L) than the normal expected values (40 to 74 µM/L) in 55% ($^{85}/_{154}$) of European breast cancer patients. Women scoring relative risks of 1.8 for breast cancer development also revealed elevated levels at 82.8 µM/L (64.6 to 98.8 µM/L) especially when compared to low risk women 70.3 µM/L (46.5 to 97.9 µM/L) and late stage metabolic syndrome with an average of 68 µM/L (47 to 95 µM/L). Patients with thyroid dysfunctions also exhibited higher levels of phenylalanine 94.6 µM/L (49.5 to 142 µM/L). As expected, cancer-free participants with cirrhosis exhibited the highest levels averaging 114.3 µM/L (84.4 to 163 µM/L).

To confirm these findings as liver-function related the inventors included cancer-free patients with HCV-induced cirrhosis (n=30) and patients with hypo (n=8) and hyperthyroidism (n=8), as thyroid dysfunction is frequently associated with liver dysfunction and with increased risk of cancer including breast. They also analyzed HIV patients due to their increased risk of cancer and the direct effect of HIV infection on liver function.

Results revealed concordance between the blood metabolic profiles of cancer-free patients with cirrhosis, thyroid dysfunction and HIV infection and the study participants at: 1) elevated relative risks of breast cancer development, 2) those with PCOS and 3) patients harboring known glandular malignancies (breast, colon, lung and liver).

The inventors divided their cancer-free group according to: i) increasing risks of cancer, ii) rising levels of gamma-glutamyl transferase (GGT) and iii) cumulative values of free-thyroxine (Free T4). The results revealed the same pattern of Gln/Glu ratios when applied to high risk women, was recapitulated in cancer-free women by progressive changes in free-T4 and GGT values. Similar to thyroid dysfunctions, elevations in blood GGT have been found to significantly increase the overall cancer risk including breast malignancies. To explore the biochemical overlap between these conditions, the inventors conducted Orthogonal Partial Least Squares Discriminative Analysis (Ortho-PLSDA) that revealed a high degree of biochemical similarity among hyper/hypothyroidism and cirrhosis patients that, together, seem to interconnect breast cancer on the one side to hematological malignancies on the opposite side.

It has previously been found that IEMs not only interfere with liver function but also affect proper endocrine physiology resulting in increased risks of diabetes, gonadal and thyroid dysfunctions.

Results of the studies identifying liver dysfunction are in agreement with the premise that breast cancer arises in an environment of fatty acid oxidation defects (FAOD). Among the most common laboratory findings in these types of IEM, in parallel with hypoglycemia, is liver dysfunction as the biochemistry of the liver is so dependent on the normal function of hepatocyte mitochondria.

The findings, therefore, resemble those associated with mitochondrial and/or peroxisomal disorders of β-oxidation, both known to be associated with the accumulation, in blood and tissues, of lipids composed of very long-chain fatty acids (VLCFA) and carnitine derivatives, the result of the inefficient oxidation of fatty acids.

In line with this concept, when controls (n=92) were compared with breast cancer patients (n=63) the untargeted mass spectrometry lipidomic data showed a global accumulation of phospholipid species containing very-long chain fatty acids (VLCFA C40) in the cancer patient specimens.

Of note are the blood elevations of lysoPC a C26:0, a biomarker routinely used in the diagnosis of peroxisomal disorders of β-oxidation. Validation of this finding was subsequently obtained by specific targeted MS/MS (p=9.07e-71, FDR=2.81e-70). Further suggestion of peroxisome as a putative subcellular location related to these metabolic findings was obtained by quantitative functional enrichment analysis (www.metaboanalyst.ca) that revealed a significant (p=1e-121) 250-fold enrichment for peroxisome localization using the metabolites L-acetylcarnitine, succinic acid, glycine, oxaloacetic acid, pyruvic acid, sarcosine, D-arginine and taurine.

An additional finding was the significant elevations of taurine in the blood of breast cancer patients and its association with cancer risk, response and survival as well as its correlation with blood levels of the oncometabolites fumarate (p=3.05e-06) and succinate (p=1.87e-05).

Both fumarate and succinate are known to increase the half-life of HIF-1 gene (hypoxia-inducible factor-1) products that sponsor angiogenesis and tumor survival (33-36).

These oncometabolites also enhance histone and DNA methylation (37, 38) leading to genome-wide epigenetic reprogramming (39). Taurine levels were also found to correlate (p=0.001, FDR=0.006) with the up-regulation of arginine methyltransferase activity, measured as the total amount of demethylated arginine residues (Total DMA).

Total DMA levels were also gradually, positively and statistically (p=5.57e-12, FDR=1.56e-11) associated with progressive stages of breast carcinogenesis.

Arginine methyltransferase activity is directly connected to MYC activity and has been reported to be associated to the state of cellular stemness.

This led to question whether the breast cancer findings were reflective of a state of cellular biochemical stemness, as it has been suggested that there are considerable parallels between human embryogenesis and cancer.

To evaluate this hypothesis, the inventors compared the breast cancer metabolomic signatures to those identified in the secretome of in-vitro fertilized, developing human embryos that were under final preparation for implantation.

Results demonstrated strong similarities between the metabolic profiles of successfully developed embryos and the biochemical phenotypes identified in women at high risk of breast cancer, those with insulin resistance and those with the shortest relapse-free survival following neoadjuvant chemotherapy.

The invention includes a new concept of carcinogenesis that incorporates an existing understanding of the genomic basis of cancer into a fundamentally different paradigm. The findings suggest that cancer "conscripts" the human genome to meet its needs under conditions of systemic metabolic stress.

Health and cancer can be seen to reflect underlying IEM-like phenotypic states that result from variable levels of mitochondrial and peroxisomal dysfunction. These dysfunctions over the course of a normal lifespan might, or might not, lead to the condition of "metabolic insufficiency" that those recognize as cancer. As one ages, the accumulation of toxic metabolites, onco-metabolites, DNA and histone methylation tips them from the state relative compensation to one of de-compensation as malignancy arises.

Described herein are blood biomarker panels based upon phenotypic features that are shared by IEM, liver and thyroid dysfunctions and cancers of glandular ancestries.

Using the identified signatures, the inventors explored correlations with other states of metabolic stress including diabetes mellitus and polycystic ovary syndrome and showed that they could recapitulate the malignant phenotype in a murine model by exposing hypoglycemic mice to exogenous insulin.

These phenotypic signatures share features of human cellular metabolic stemness and suggest that the same metabolic cascades that sponsor successful embryogenesis, a paradigm of stemness, are shared or re-activated, systemically, during periods of insulin/glucose imbalance.

The described metabolic stresses would, in the majority of the population, be counteracted by the up-regulation of gluconeogenesis and fatty acid oxidation. However, persons manifesting IEM-like phenotypes may be unable to marshal these critical responses, leading to the aberrant dependence upon MYC-related metabolic reprogramming.

This would reflect an underlying "tendency" to malignant transformation unleashed by stressors, that in breast cancer are "uncovered" by exacerbating risk factors, such as nulliparity, obesity and lifestyle but which only become manifest in those pre-disposed women who carry the features of inborn-priming.

The finding that the metabolic phenotype identified in the blood and tumor tissue of colon cancer patients is identical to the signature found in those same patients' normal colonic mucosa supports the hypothesis that cancer arises as a local manifestation of a state a systemic metabolic insufficiency.

Variable levels of metabolic stress, therefore, would be different from individual to individual depending on inherited, mild to moderate metabolic deficiencies, reminiscent of IEM, but not severe enough to cause disease during much of life.

These signatures identify clinical breast cancer irrespective of stage, histology, intrinsic subtype, BMI, menopausal status or age with an accuracy of 95%, and are also shown to predict tumor response to neoadjuvant chemotherapy and overall survival.

The clinical implications of these findings are several and include the development of a new diagnostic test for the early detection of breast cancer and its application for prognosis and the prediction of response. The findings may also apply to other cancers of glandular histology. More importantly, the results reflect the application of a phenotypic signature that can dovetail nicely with advances in genomics, transcriptomics and proteomics as we strive for a more global understanding of human illness.

In conclusion, the invention includes phenotypic evidence supporting the hypothesis that cancers of glandular ancestry, particularly breast cancer, represent the end result of pre-existing metabolic perturbations associated with a MYC-induced systemic condition: Cancer as a metabolic epiphenomenon.

Ovary Cancer Signature

Ovary cancer today is recognized as a type of malignancy originated, in the majority of times, from its surrounding tissues, particularly the fimbria, the very external end of the fallopian tube. The American Cancer Society estimates that in the United States, for 2018, there are about 22,240 new cases, out of which, more than 50% (14,070) of women will die from this disease. Ovarian cancer, therefore, is accounting for more deaths than any other cancer of the female reproductive system. This cancer mainly develops in 63 years or older women and it is more common in white than African-American women.

Ovarian cancer is difficult to detect, especially in the early stages. This is partly due to the fact that the ovaries—two small, almond-shaped organs on either side of the uterus—are deep within the abdominal cavity.

Fewer than one-half of women diagnosed with ovarian cancer survive longer than 5 years, and although the 5-year survival of patients with localized ovarian cancer is greater than 90%, only 15% of all women are diagnosed with localized disease.

Currently, no organization recommends screening average-risk women for ovarian cancer. Nevertheless, screening and diagnostic methods for ovarian cancer include pelvic examination, cancer antigen 125 (CA 125) as a tumor marker, transvaginal ultrasound (TVU), and potentially multimarker panels and bioinformatic analysis of proteomic patterns.

However, the performance of these tests for screening when used alone or in combination has been poor. The sensitivity and specificity of pelvic examination for the detection of asymptomatic ovarian cancer are poor and do not support physical examination as a screening method. CA 125 has limited sensitivity and specificity, as does TVU when used independently or in combination.

In 2011, the Prostate Lung Colorectal and Ovarian (PLCO) initiative concluded, with regards of ovarian cancer screening, that there was adequate evidence that annual screening with CA 125 and TVU does not reduce ovarian cancer mortality, and that, there was adequate evidence that screening for ovarian cancer can lead to important harms, mainly surgical interventions in women without ovarian cancer.

Therefore, an urgent need exists in the art for new and highly sensitive screening procedures, preferably less demanding without the need of several specialized equipment and personnel or resources.

In view of the above-mentioned problems existing in the art, the object underlying the present invention is the provision of new biomarkers for assessing ovary cancer, which allows for screening of ovary cancer in an early stage of disease progression with high accuracy and reliability.

Optimally, the marker should be easily detectable in a biological sample such as in blood and its level should be consistently related to the stage of ovary cancer. Moreover, it is an object of the present invention to provide for a method for assessing ovary cancer in a biological sample, which allows for fast, convenient and high throughput performance.

In order to solve the objects underlying the present invention the inventors based their investigations on metabolomics as it could give insight in the biochemical changes occurring in the course of ovary cancer development and offer several novel and potentially better biomarkers.

The invention is an early-diagnosis-tool that identifies patients with ovarian cancer in its earliest stages, when intervention offers the highest possibility of cure. The invention provides prognostic information and serves as a predictive test for clinical response and survival.

The inventors found that a more comprehensive picture of all metabolomics pathways and mechanisms involved in ovary cancer is given when using a panel of metabolites that are altered in parallel of cancer rather than employing the screening techniques performed in the art, such as ultrasound.

Therefore, the present invention provides for never described biomarkers (i.e. a new biomarker set) suitable for assessing ovary cancer, including early and more advanced stages of disease and also provides biomarker sets that clearly discriminate, at baseline, patients with elevated risk of relapse after initial treatment.

Moreover, the present invention also provides for a method for assessing ovary cancer in a mammalian subject that was achieved and developed taking into consideration comprehensive and extensive comparisons not only with several other malignancies but also with several metabolic benign conditions and, therefore, can be considered as the closest stage of an ideal tumor marker.

In particular, the application of targeted quantitative mass spectrometry (MS/MS) to the blood of ovarian cancer patients led to the creation of a metabolic signature that provides clinically validated diagnostic and prognostic information for women with ovarian cancer and those at risk for the disease.

Targeted, quantitative MS/MS provides annotated blood concentrations of metabolites that are essential for the accurate determination of clinically relevant metabolic signatures. Individual metabolite concentrations and qualitative, non-targeted, measures do not provide the necessary rigor that is required for the accurate identification of cancer-related metabolic perturbations.

In a first embodiment, the biomarkers and biomarker sets of the present invention are used for screening of subjects, such as human patients, potentially suffering from ovary cancer and diagnosis of ovary cancer in these subjects.

It has surprisingly been found in the present invention that the biomarkers and biomarker sets as described herein are particularly useful for fast, easy and high throughput screening of a large number of subjects, such as human patients, and for diagnosis of ovary cancer from blood samples of these subjects with improved accuracy of results.

Although accuracy and reliability of screening and/or diagnosis, as determined by the parameters of one or more of specificity, sensitivity, PPV and NPV, by using the above-specified biomarker combination is already greatly improved compared with the prior art techniques, such as ultrasound, the accuracy and reliability can be further improved by using one or more, preferably two or more, further preferably three or more additional metabolites.

Hence, in a preferred embodiment the biomarker set further comprises one or more additional amino acid, such as those included in FIG. 2. The additional amino acids are preferably selected from glucogenic/ketogenic amino acids such as glycine, cysteine, alanine, arginine, proline, aspartate, asparagine, methionine, isoleucine, leucine, lysine, threonine phenylalanine, tyrosine and tryptophan, most preferably asparagine and aspartate.

Moreover, the lipid is preferably selected from sphingolipids and glycerolipids, such as glycerophospholipids, e.g. one or more of the lipids included in FIGS. 4-6.

Further preferably, the lipid is derived from arachidonic acid, preferably arachidonic acid derived lipids containing 36 or more carbon atoms, and most preferably is selected from arachidonic polyunsaturated phosphatidylcholine acyl-alkyl or acyl-acyl, arachidonic mono-unsaturated phosphatidylcholine acyl-alkyl or acyl-acyl and arachidonic saturated phosphatidylcholine acyl-alkyl or acyl-acyl.

In a further preferred embodiment, the combination of metabolites further comprises one or more of lipids described in FIGS. 4-6 and one or more acylcarnitines as well as carnitine (C0) described in FIG. 3.

As the method of this embodiment can be performed from blood samples, the method greatly increases the subject's compliance compared to prior art screening techniques, such as ultrasound. In particular, the method greatly increases reliability and sensitivity of the screening results, in particular reduces the number of false positive and false negative results, and is less time consuming, and thus can be performed with a high number of patients.

Figures 12A, 12B:
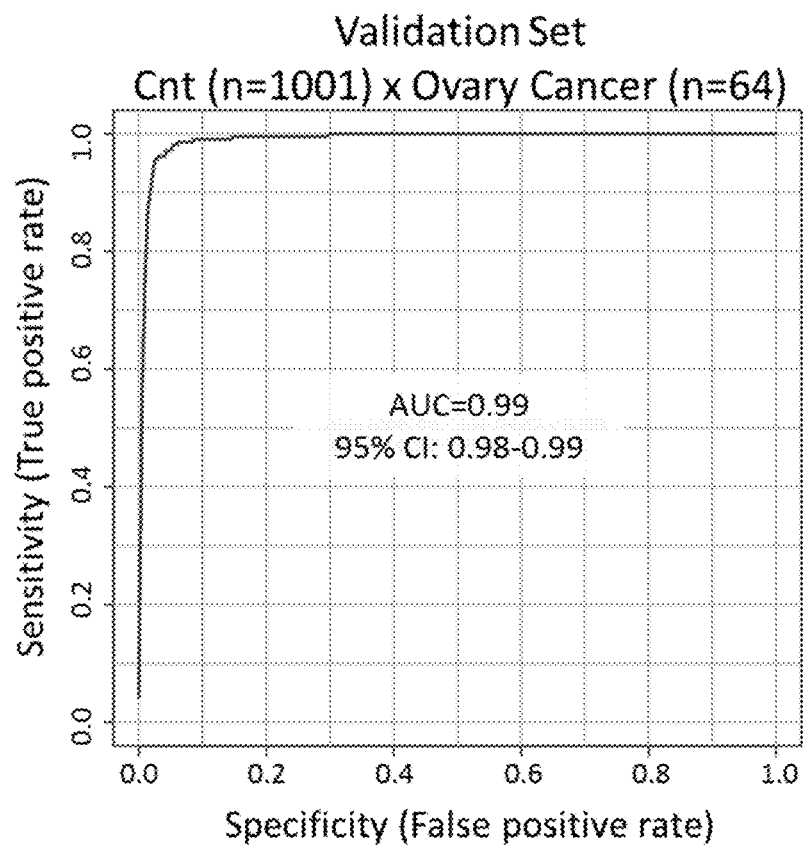
FIGS. 12A and B provide, respectively, a multivariable ROC curve analysis for ovarian cancer, along with performance characteristics for the same.

This can be seen, for example, in FIGS. 12A and B, showing that the signatures developed for assessing ovarian cancer (i.e., one embodiment of the present invention) have a sensitivity of 98.46%, a specificity of 96.62%, and a negative predictive value of 99.90%. In particular, FIG. 12A shows a multivariate ROC curve analysis for ovary cancer patients (n-64) compared to healthy participants as well as other malignant and non-malignant conditions (n=1001). FIG. 12B depicts the performance of the identified metabolites and ratios for ovary cancer patients. The near 100% negative predictive value (99.90%) makes the present test highly indicative as a powerful screening tool.

Figure 13:
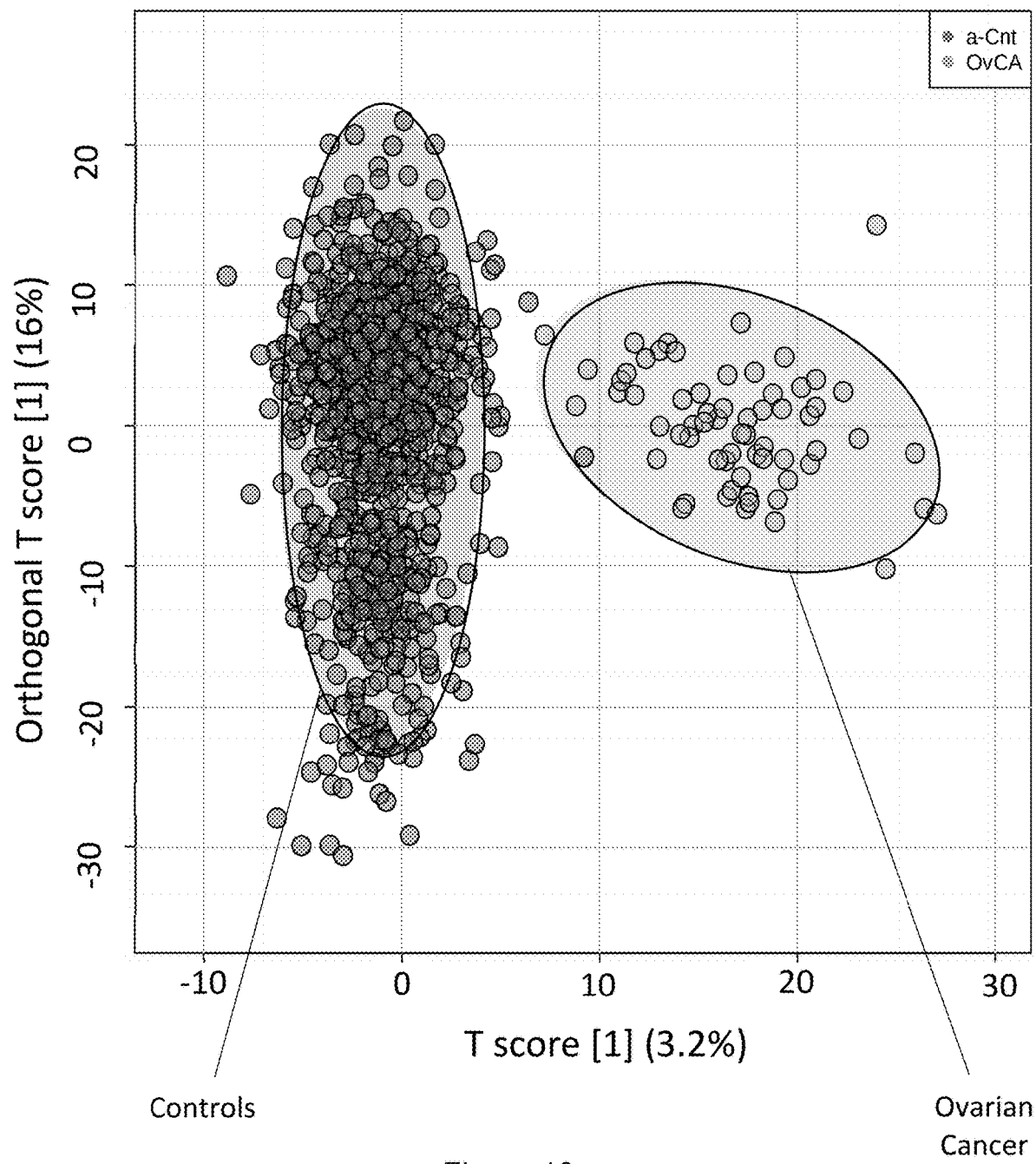
FIG. 13 provides an Ortho-PLSDA Score's plot for ovary cancer patients compared to healthy participants and other malignant and non-malignant conditions.
Figure 14A:
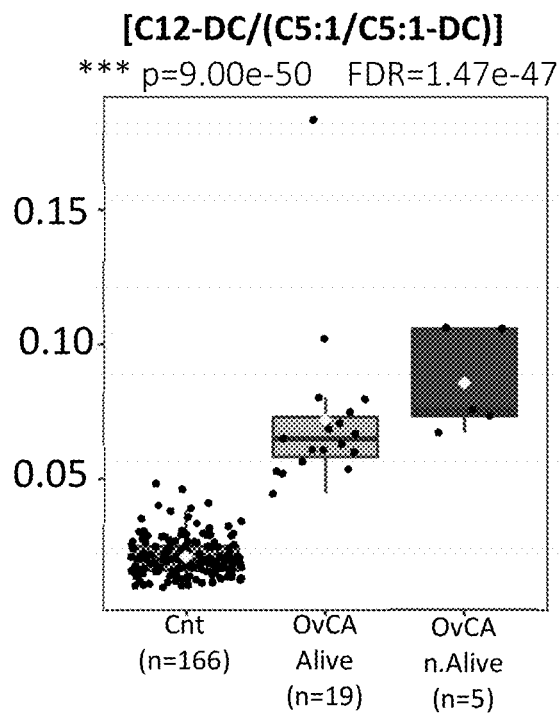
FIGS. 14A-D illustrate certain ratios that are useful in determining a survival rate (prognoses) for ovary cancer patients.
Figure 14B:
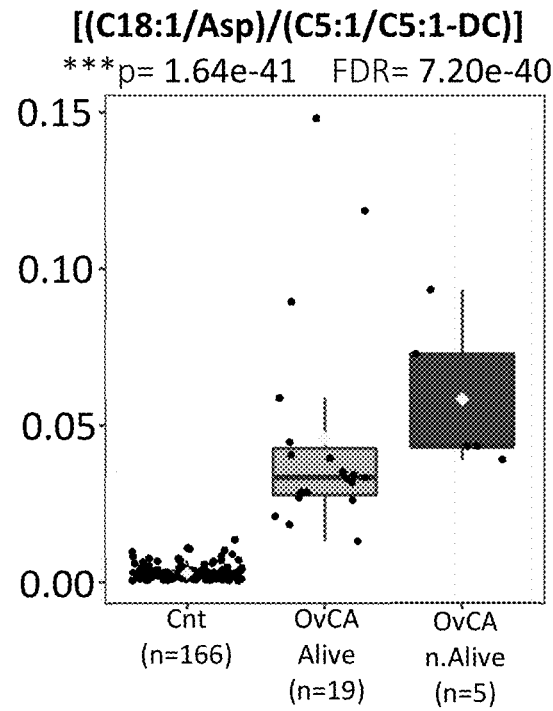
Figure 14C:
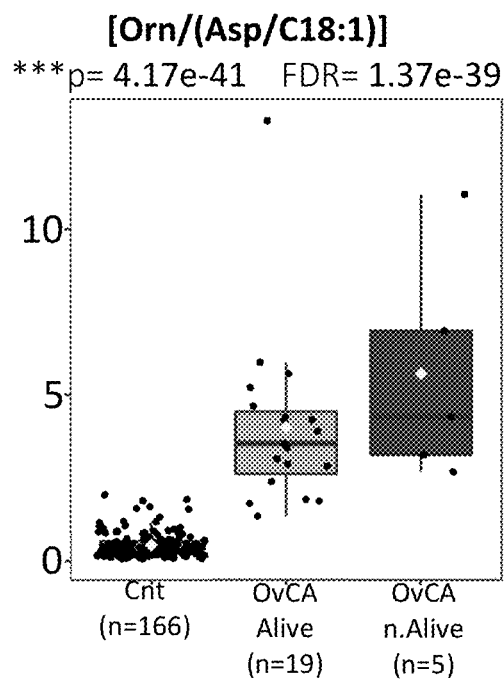
Figure 14D:
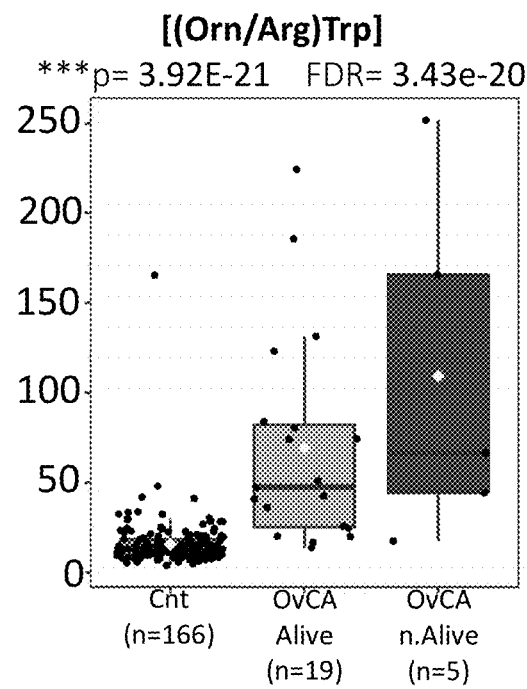

FIG. 13 shows an Ortho-PLSDA Score's plot of ovary cancer patients (n=64) compared to healthy participants as well as other malignant and non-malignant conditions (n=1001). By processing (e.g., isolating, quantifying, normalizing, etc.) each sample (e.g., blood sample), and then plotting the initial results (e.g., using an Ortho-PLSDA Score's plot) based on at least one ovarian cancer signature (as identified by the inventors), each patient clearly falls within (a) the control group or (b) the ovarian cancer group.

Moreover, portions of the signature provide details on each patient's prognosis. This can be seen, for example, in FIGS. 14A-D, where various equations (identified at the top of each chart) provide survival rate (prognosis) information for each patient. Thus, not only have the inventors identified signatures that can be used to diagnosis ovarian cancer, but also to prognose ovarian cancer. It should be appreciated that while the charts provided in FIGS. 13 and 14A-D illustrate (a) diagnosis for ovarian cancer and (b) survival rates, the present invention is not so limited, and the ovarian signatures (or portions thereof) can be used to provide other assessments for ovarian cancer, including screening for, diagnosing, prognosing, treating the same as discussed in greater detail in the results section below.

A preferred signature (or portions thereof) for assessing ovarian cancer is provided in FIG. 15, including a core ovarian cancer equation, metabolite enhancers, ratio enhancers, and core equations with enhancers. As can be seen in FIG. 15, the core ovarian cancer equation is (C5:1/C5:1-DC), or a ratio of Tiglylcarnitine to Glutaconylcarnitine (see FIG. 3). The inventors have discovered that this ratio of individual metabolites, after quantification, normalization, etc., are critical in assessing a patient for ovarian cancer. Other key portions include [Orn/(AspdC18:1)] (where "d" is divided by, i.e., Asp/C18:1)), [(Orn/Arg)Trp], [C12-DC/(C5:1/C5:1-DC)], and [(C18:1/Asp)/(C5:1/C5:1-DC)], which can be used to not only diagnose, but prognose for ovarian cancer.

While not a limitation of the present invention, targeted metabolomic analysis of plasma and tissue samples may be performed using the Biocrates Absolute-IDQ P180 (BIOCRATES, Life Science AG, Innsbruck, Austria). This validated targeted assay allows for simultaneous detection and quantification of metabolites in plasma and tissue samples in a high-throughput manner.

As discussed in the breast cancer—patients and methodology section, absolute quantification (µmol/L) of blood metabolites may be achieved by targeted quantitative profiling of 186 annotated metabolites by electrospray ionization (ESI) tandem mass spectrometry (MS/MS) in a plurality of biological samples. The process described in that section is equality applicable here, where a targeted profiling scheme is used to quantitatively screen for fully annotated metabolites, an xls file is generated, which includes sample identification and 186 metabolite names and concentrations with the unit of µmol/L of plasma, and log-transformation is applied to all quantified metabolites to normalize the concentration distributions and processed. ROC curves are then generated, and significant feature are used to build classification models.

In total, 186 annotated metabolites were quantified using the p180 kit (BIOCRATES Life Sciences AG, Innsbruck, Austria), including the ones described in the breast cancer—patients and methodology section. As well, groups of metabolites related to specific functions were assembled as ratios, and other mathematical relationships were observed (as discussed above) (e.g., summing of levels of amino acids, summing total acylcarnitines, proportions among sums of saturated, monounsaturated and polyunsaturated structural lipids, etc.). See discussion above in the breast cancer—patient and methodology section.

With respect to ovarian cancer, samples were injected into a Shimadzu Prominence LC system coupled to an AB-Sciex 5600 Triple TOF mass spectrometer instrument with an acquisition scan rate of 100 spectra/sec and stable mass accuracy of ~2 ppm. Flow Injection Analysis (FIA) was performed using isocratic elution with Methanol/Water (90/10) with 5.0 mM of ammonium formate. Flow rate and injection volumes were 0.025 mL/min and 50 µL respectively.

No ion source or declustering potential (50 V and −40 V) optimization was performed. The following ionization parameters were applied: CUR=20 psi, GS1=20 psi, GS2=15 psi, Temp=250° C., IS=5000 V (−4000V). MS scan ranging from m/z 100 to 1200 with accumulation time of 0.25 s and product ion scan from m/z 100 to 1200 and accumulation time of 0.03 s are the adopted parameters during survey and dependent scans respectively.

Specific parameters defining the presence of ovarian cancer using targeted quantitative MS/MS are provided in FIG. 8. Specific metabolic ratios defining presence of ovarian cancer using targeted quantitative MS/MS are provided in FIG. 9.

When the metabolic profiles of patients with different tumors (lung, colon, liver, leukemias, lymphomas and squamous cells carcinoma of head and neck) were examined, the results demonstrated enhanced glutamine consumption, particularly in patients harboring tumors of glandular ancestries. Extending these studies to include patients with polycystic ovary syndrome (PCOS), cirrhosis, high-risk of breast cancer and stage 5 metabolic syndrome revealed that these cancer-free participants manifested glutaminolytic profiles that were very similar to those found in adenocarcinoma patients.

The ratio (Glu/Hexoses) was assembled, following the in vitro demonstration of the "glutamate pulling effect," where glucose starvation in malignant cells culture leads to elevations in glutamate through a MYC-coordinated reaction. This effect was clearly identified in the blood of patients harboring adenocarcinomas, those at higher risk of breast cancer and individuals with PCOS. Noteworthy, neither of the control groups composed of population-based normal controls or patients with non-glandular tumors (leukemias, lymphomas, multiple myelomas and squamous cell carcinomas) revealed marked changes in this ratio particularly squamous cell carcinomas that revealed similar levels to controls. Increases in the "glutamate pulling effect" have been described under conditions of metabolic stress induced by glucose deprivation.

In agreement, the inventors found a significant (p=0.003, FDR=0.009) inverse correlation between patient blood hexoses concentrations and the values of our breast cancer equation {[PC aa 36:6/[(Val/Phe)/Taurine]/C10:2}. In line with the premise that glandular cancers are promoted under conditions of relative hypoglycemia, measured as the "glutamate pulling effect," their results suggest that the isolated determination of blood glucose levels may not be as informative as the measurement of hexose levels in relation to other metabolic intermediates including: i) the mitochondrial carnitine palmitoyltransferase II (CPT-2) deficiency ratio (C16/C3), ii) the peroxisomal impairment biomarkers lysoPC a C26:0, lysoPC a C26:1 and lysoPC a C28:1, or iii) its relation to glutaminolysis [Phe/(Gln/Glu)/Asp].

Importantly, both CPT-2 and peroxisomal deficiencies, well known inborn errors of metabolism, are associated with hypoglycemia in afflicted patients. If a state of relative hypoglycemia were to occur in ovary cancer as the result of inborn-like errors of metabolism then hyperinsulinemia associated with chronic hypoglycemia would constitute a powerful metabolic stressor capable of systemically up-regulating glycolysis and glutaminolysis, even in the absence of cancer.

In sum, carcinogenesis is a complex, polygenic process that draws upon numerous altered cellular functions leading ultimately, over decades, to a state of irreversible malignant transformation. Molecular signatures as static measures cannot capture the dynamic nature of biological processes as they fail to encompass the complexity, redundancy and promiscuity of these events.

Malignant transformation demands that cells successfully traverse metabolic, structural and immune evasive strategies. This methodology uses a multi-dimensional invention to define malignant transformation as a metabolic signature.

This invention uses targeted quantitative MS/MS, to define unique and previously unknown relationships between bio-energetic, biosynthetic and immune phenotypes in patients with ovarian cancer. This signature defines the ovarian cancer phenotype and is applied to diagnose and provide prognostic information for patients with ovarian cancer and those at risk for the development of ovarian cancer.

The invention extends to other malignancies as there are commonalities between ovarian cancers and other tumor types, and is applicable to urine and saliva, as these body fluids represent additional sources of material for the assessment of the metabolic signatures defined in blood.

Colorectal Cancer (CRC) Signature

Colorectal cancer is the third most common malignancy diagnosed in both men and women in the United States and according to the American Cancer Society estimates, a total of 101,523 CRC new cases are expected for the upcoming year, being 97,220 of colon and 43,030 of rectal cancer.

Overall, the lifetime risk of developing colorectal cancer is: about 1 in 22 (4.49%) for men and 1 in 24 (4.15%) for women being the third leading cause of cancer-related deaths in the United States.

Currently there are 3 in vitro diagnosis (IVD) tests that are routinely used for CRC screening, the fecal immunochemical test (FIT), the fecal-based DNA test and the blood-based DNA test (the SEPT9 assay). FIT tests, that replaced the old fecal occult blood tests (FOBT), exhibited satisfactory sensitivity (79%) and specificity (94%) with low costs and therefore become the major screening test for CRC at the moment.

The sensitivity of the fecal DNA test appeared to be very high due to combination of multiple methods while its high cost is an obstacle preventing the test from broad use. Both sensitivity and specificity for the SEPT9 test in CRC screening were lower than those of the FIT and fecal DNA test, but it showed high compliance with promising future if its accuracy can be improved.

Combined tests with multiple markers should be a future direction in CRC screening, however, some hurdles, such as technical integration, test/interpretation optimization, and high costs, etc, need to be overcome before they can be used in large-scale CRC screening aiming at asymptomatic average-risk population.

CEA and carbohydrate antigen 199 (CA199) are the two most common serum-based glycoprotein CRC markers, however, they are not appropriate for CRC screening due to their low sensitivity and the lack of CRC specificity, especially for early-stage CRC.

For example, CEA test exhibited a sensitivity of 40.9%-51.8% and a specificity of 85.2%-95% for CRC detection in three studies. Therefore, it is more appropriate to be used in monitoring the CRC recurrence or response from patients to surgical or systemic therapy, rather than screening. The main drawback of serum glycoprotein markers in CRC screening is that the sensitivity and specificity of any single marker is not high enough to make it a reliable indicator.

In view of the above-mentioned problems existing in the art, the object underlying the present invention is the provision of new biomarkers for assessing colorectal cancer, which allows for screening of colorectal cancer in an early stage of disease progression with high accuracy and reliability.

Optimally, the marker should be easily detectable in a biological sample such as in blood and its level should be consistently related to the stage of colorectal cancer. Moreover, it is an object of the present invention to provide for a method for assessing colorectal cancer in a biological sample, which allows for fast, convenient and high throughput performance.

In order to solve the objects underlying the present invention the inventors based their investigations on metabolomics as it could give insight in the biochemical changes occurring in the course of colorectal cancer development and offer several novel and potentially better biomarkers.

The inventors found that a more comprehensive picture of all metabolomics pathways and mechanisms involved in colorectal cancer is given when using a panel of metabolites that are altered in parallel of cancer rather than employing the screening techniques performed in the art, such as ultrasound.

Therefore, in one embodiment of the present invention, never described biomarkers (i.e. a new biomarker set) are provided suitable for assessing colorectal cancer, including early and more advanced stages of disease. Also included are biomarker sets that clearly discriminate, at baseline, patients with elevated risk of relapse after initial treatment.

Moreover, the present invention also provides for a method for assessing colorectal cancer in a mammalian subject that was achieved and developed taking into consideration comprehensive and extensive comparisons not only with several other malignancies but also with several metabolic benign conditions and, therefore, can be considered as the closest stage of an ideal tumor marker.

In a first embodiment, the biomarkers and biomarker sets of the present invention are used for screening of subjects, such as human patients, potentially suffering from colorectal cancer and diagnosis of colorectal cancer in these subjects.

It has surprisingly been found in the present invention that the biomarkers and biomarker sets as described herein are particularly useful for fast, easy and high throughput screening of a large number of subjects, such as human patients, and for diagnosis of colorectal cancer from blood samples of these subjects with improved accuracy of results.

Although accuracy and reliability of screening and/or diagnosis, as determined by the parameters of one or more of specificity, sensitivity, PPV and NPV, by using the above-specified biomarker combination is already greatly improved compared with the prior art techniques, such as ultrasound, the accuracy and reliability can be further improved by using one or more, preferably two or more, further preferably three or more additional metabolites.

Hence, in a preferred embodiment the biomarker set further comprises one or more additional amino acid, such as those included in FIG. 2. The additional amino acids are preferably selected from glucogenic/ketogenic amino acids such as glycine, cysteine, alanine, arginine, proline, aspartate, asparagine, methionine, isoleucine, leucine, lysine, threonine phenylalanine, tyrosine and tryptophan, most preferably asparagine and aspartate.

Moreover, the lipid is preferably selected from sphingolipids and glycerolipids, such as glycerophospholipids, e.g. one or more of the lipids included in FIGS. 4-6.

Further preferably, the lipid is derived from arachidonic acid, preferably arachidonic acid derived lipids containing 36 or more carbon atoms, and most preferably is selected from arachidonic polyunsaturated phosphatidylcholine acyl-alkyl or acyl-acyl, arachidonic mono-unsaturated phosphatidylcholine acyl-alkyl or acyl-acyl and arachidonic saturated phosphatidylcholine acyl-alkyl or acyl-acyl.

In a further preferred embodiment, the combination of metabolites further comprises one or more of lipids described in FIGS. 4-6 and one or more acylcarnitines as well as carnitine (C0) described in FIG. 3.

As the method of this embodiment can be performed from blood samples, the method greatly increases the subject's compliance compared to prior art screening techniques, such as ultrasound. In particular, the method greatly increases reliability and sensitivity of the screening results, in particular reduces the number of false positive and false negative results, and is less time consuming, and thus can be performed with a high number of patients.

Figures 16A, 16B:
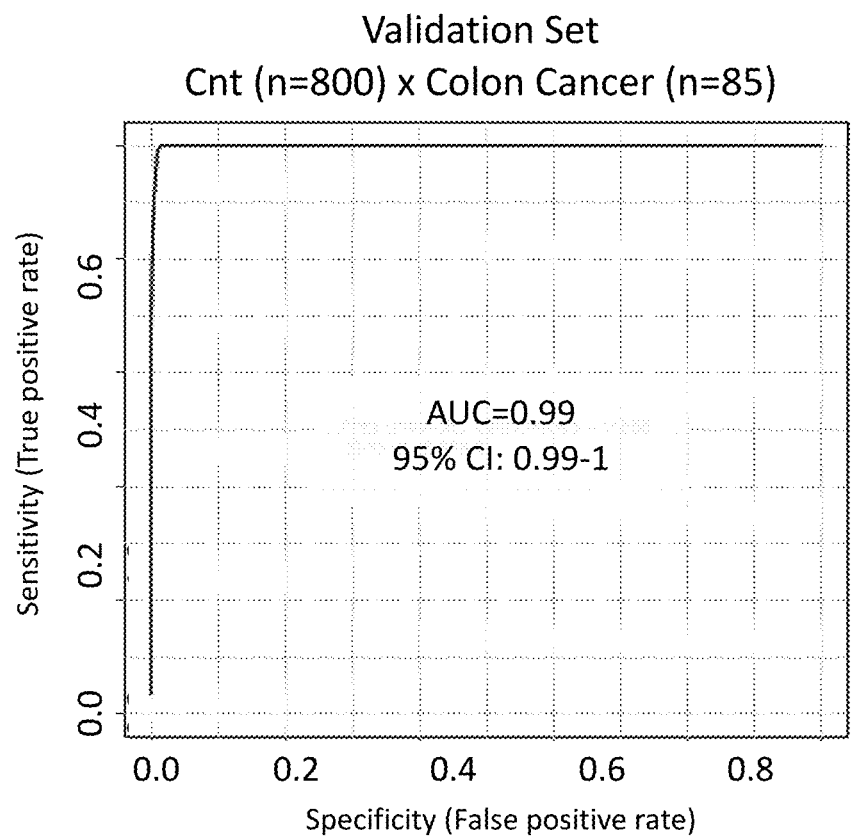
FIGS. 16A and B provide, respectively, a multivariable ROC curve analysis for colon cancer, along with performance characteristics for the same.

This can be seen, for example, in FIGS. 16A and B, showing that the signatures developed for assessing colon cancer (i.e., one embodiment of the present invention) have a sensitivity of 98.84%, a specificity of 98.40%, and a negative predictive value of 99.88%. In particular, FIG. 16A shows a multivariate ROC curve analysis for colon cancer patients (n-85) compared to healthy participants as well as other malignant and non-malignant conditions (n=800). FIG. 16B depicts the performance of the identified metabolites and ratios for colon cancer patients. The near 100% negative predictive value (99.88%) makes the present test highly indicative as a powerful screening tool.

Figure 17:
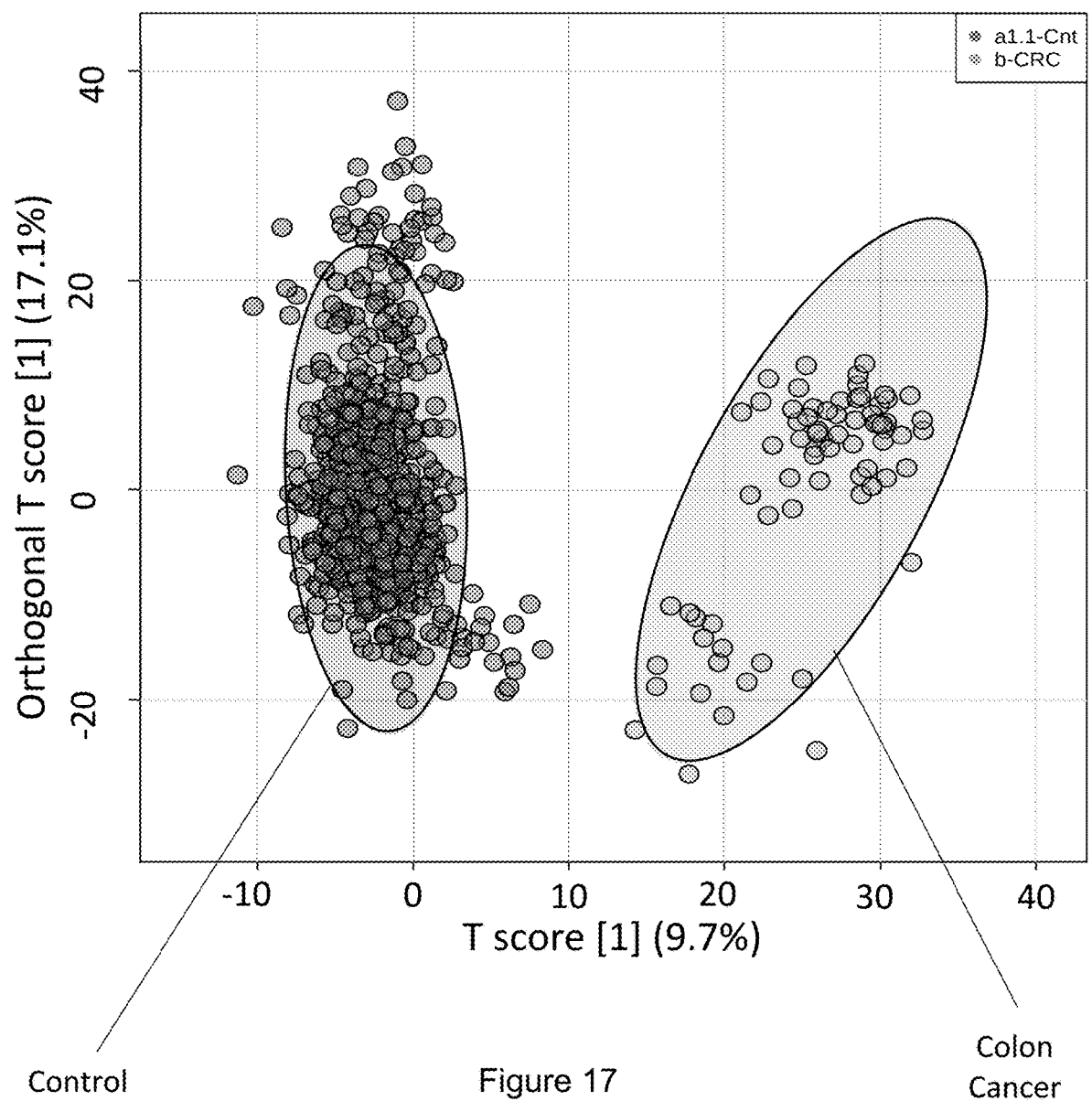
FIG. 17 provides an Ortho-PLSDA Score's plot for colon cancer patients compared to healthy participants and other malignant and non-malignant conditions.
Figure 18A:
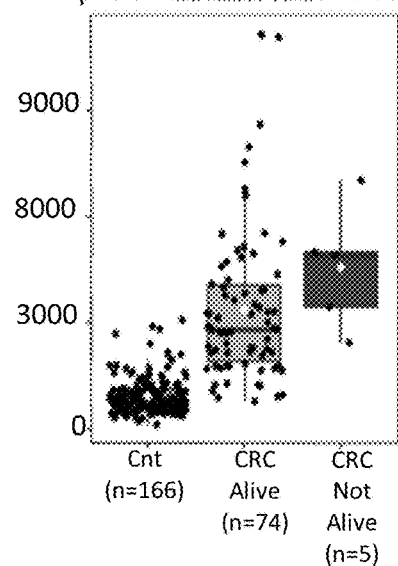
FIGS. 18A-C illustrate certain ratios that are useful in determining a survival rate (prognoses) for colon cancer patients.
Figure 18B:
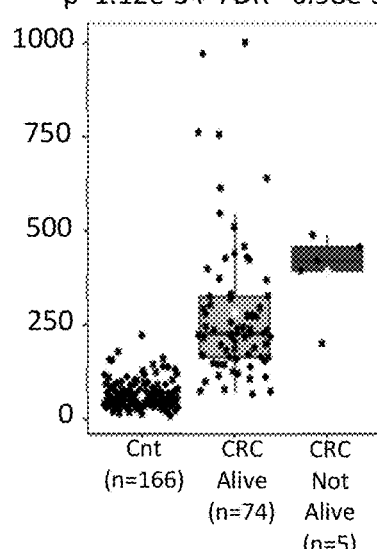
Figure 18C:
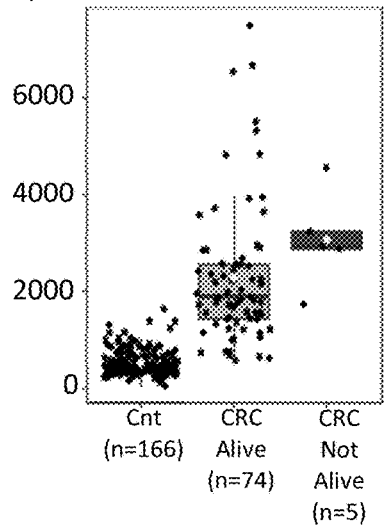

FIG. 17 shows an Ortho-PLSDA Score's plot of colon cancer patients (n=85) compared to healthy participants as well as other malignant and non-malignant conditions (n=800). By processing (e.g., isolating, quantifying, normalizing, etc.) each sample (e.g., blood sample), and then plotting the initial results (e.g., using an Ortho-PLSDA Score's plot) based on at least one colon cancer signature (as identified by the inventors), each patient clearly falls within (a) the control group or (b) the colon cancer group.

Moreover, portions of the signature provide details on each patient's prognosis. This can be seen, for example, in FIGS. 18A-C, where various equations (identified at the top of each chart) provide survival rate (prognosis) information for each patient. Thus, not only have the inventors identified signatures that can be used to diagnosis colon cancer, but also to prognose colon cancer. It should be appreciated that while the charts provided in FIGS. 17 and 18A-C illustrate (a) diagnosis for colon cancer and (b) survival rates, the present invention is not so limited, and the colon signatures (or portions thereof) can be used to provide other assessments for colon cancer, including screening for, diagnosing, prognosing, treating the same as discussed in greater detail in the results section below.

Figures 19, 20A:
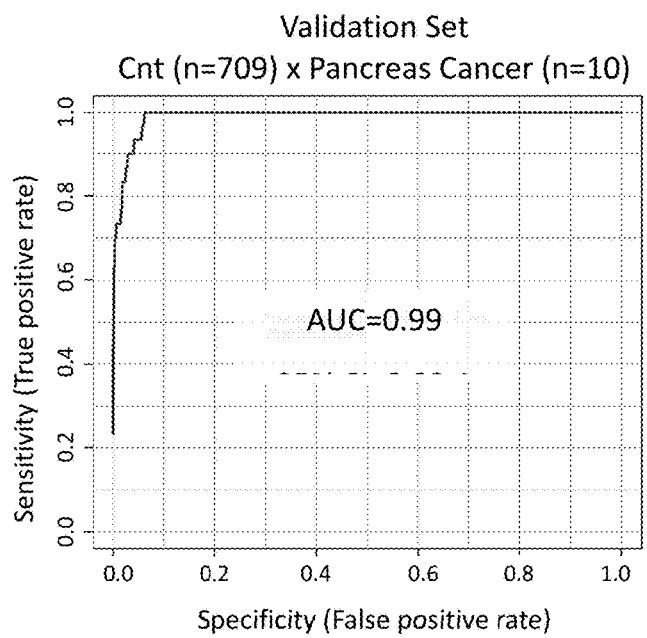
FIG. 19 provides metabolites and mathematical derivatives thereof (e.g., ratios, etc.) that are used in one embodiment of the present invention to assess (e.g., diagnose, prognose, etc.) colon cancer in a patient.
FIGS. 20A and B provide, respectively, a multivariable ROC curve analysis for pancreatic cancer, along with performance characteristics for the same.

A preferred signature (or portions thereof) for assessing colon cancer is provided in FIG. 19, including a core ovarian cancer equation, metabolite enhancers, and core equations with enhancers. As can be seen in FIG. 19, the core ovarian cancer equation is (C16:1/PC aa C34:2), or a ratio of Hexadecenoylcarnitine to Phosphatidylcholine with diacyl residue sum (see FIGS. 3 and 5). The inventors have discovered that this ratio of individual metabolites, after quantification, normalization, etc., are critical in assessing a patient for colon cancer. Other key portions include {SM C20:2/[(C16:1/PC aa C34:2)/C5:1-DC]}, {SM OH C16:1/[(C16:1/PC aa C34:2)/C5:1-DC]}, and {SM OH C14:1/[(C16:1/PC aa C34:2)/C5:1-DC]}, which can be used to not only diagnose, but prognose for colon cancer.

Pancreatic Cancer Signature

Pancreatic cancer arises when cells in the pancreas, a glandular organ behind the stomach, begin to multiply out of control and form a mass. These cancerous cells can invade other parts of the body. There are usually no symptoms in the disease's early stages, and symptoms that are specific enough to suggest pancreatic cancer typically do not develop until the disease has reached an advanced stage. By the time of diagnosis, pancreatic cancer has often spread to other parts of the body.

In 2015, pancreatic cancers of all types resulted in 411,600 deaths globally. Pancreatic cancer is the fifth most common cause of death from cancer in the United Kingdom, and the third most common in the United States. The disease occurs most often in the developed world, where about 70% of the new cases in 2012 originated. Pancreatic adenocarcinoma typically has a very poor prognosis: after diagnosis, 25% of people survive one year and 5% live for five years. For cancers diagnosed early, the five-year survival rate rises to about 20%.

Pancreatic cancer is usually diagnosed by a combination of medical imaging techniques such as ultrasound or computed tomography, blood tests, and examination of tissue samples (biopsy). The disease is divided into stages, from early (stage I) to late (stage IV). Screening the general population has not been found to be effective.

In view of the above-mentioned problems existing in the art, the object underlying the present invention is the provision of new biomarkers for assessing pancreatic cancer, which allows for screening of pancreatic cancer in an early stage of disease progression with high accuracy and reliability.

Optimally, the marker should be easily detectable in a biological sample such as in blood and its level should be consistently related to the stage of pancreatic cancer. Moreover, it is an object of the present invention to provide for a method for assessing pancreatic cancer in a biological sample, which allows for fast, convenient and high throughput performance.

In order to solve the objects underlying the present invention the inventors based their investigations on metabolomics as it could give insight in the biochemical changes occurring in the course of pancreatic cancer development and offer several novel and potentially better biomarkers.

The inventors found that a more comprehensive picture of all metabolomics pathways and mechanisms involved in pancreatic cancer is given when using a panel of metabolites that are altered in parallel of cancer rather than employing the screening techniques performed in the art, such as ultrasound or computed tomography.

Therefore, in one embodiment of the present invention, never described biomarkers (i.e. a new biomarker set) are provided suitable for assessing pancreatic cancer, including early and more advanced stages of disease. Also included are biomarker sets that clearly discriminate, at baseline, patients with elevated risk of relapse after initial treatment.

Moreover, the present invention also provides for a method for assessing pancreatic cancer in a mammalian subject that was achieved and developed taking into consideration comprehensive and extensive comparisons not only with several other malignancies but also with several metabolic benign conditions and, therefore, can be considered as the closest stage of an ideal tumor marker.

In a first embodiment, the biomarkers and biomarker sets of the present invention are used for screening of subjects, such as human patients, potentially suffering from pancreatic cancer and diagnosis of pancreatic cancer in these subjects.

It has surprisingly been found in the present invention that the biomarkers and biomarker sets as described herein are particularly useful for fast, easy and high throughput screening of a large number of subjects, such as human patients, and for diagnosis of pancreatic cancer from blood samples of these subjects with improved accuracy of results.

Although accuracy and reliability of screening and/or diagnosis, as determined by the parameters of one or more of specificity, sensitivity, PPV and NPV, by using the above-specified biomarker combination is already greatly improved compared with the prior art techniques, such as ultrasound, the accuracy and reliability can be further improved by using one or more, preferably two or more, further preferably three or more additional metabolites.

Hence, in a preferred embodiment the biomarker set further comprises one or more additional amino acid, such as those included in FIG. 2. The additional amino acids are preferably selected from glucogenic/ketogenic amino acids such as glycine, cysteine, alanine, arginine, proline, aspartate, asparagine, methionine, isoleucine, leucine, lysine, threonine phenylalanine, tyrosine and tryptophan, most preferably asparagine and aspartate.

Moreover, the lipid is preferably selected from sphingolipids and glycerolipids, such as glycerophospholipids, e.g. one or more of the lipids included in FIGS. 4-6.

Further preferably, the lipid is derived from arachidonic acid, preferably arachidonic acid derived lipids containing 36 or more carbon atoms, and most preferably is selected from arachidonic polyunsaturated phosphatidylcholine acyl-alkyl or acyl-acyl, arachidonic mono-unsaturated phosphatidylcholine acyl-alkyl or acyl-acyl and arachidonic saturated phosphatidylcholine acyl-alkyl or acyl-acyl.

In a further preferred embodiment, the combination of metabolites further comprises one or more of lipids described in FIGS. 4-6 and one or more acylcarnitines as well as carnitine (C0) described in FIG. 3.

As the method of this embodiment can be performed from blood samples, the method greatly increases the subject's compliance compared to prior art screening techniques. In particular, the method greatly increases reliability and sensitivity of the screening results, in particular reduces the number of false positive and false negative results, and is less time consuming, and thus can be performed with a high number of patients.

Figures 20B, 21:
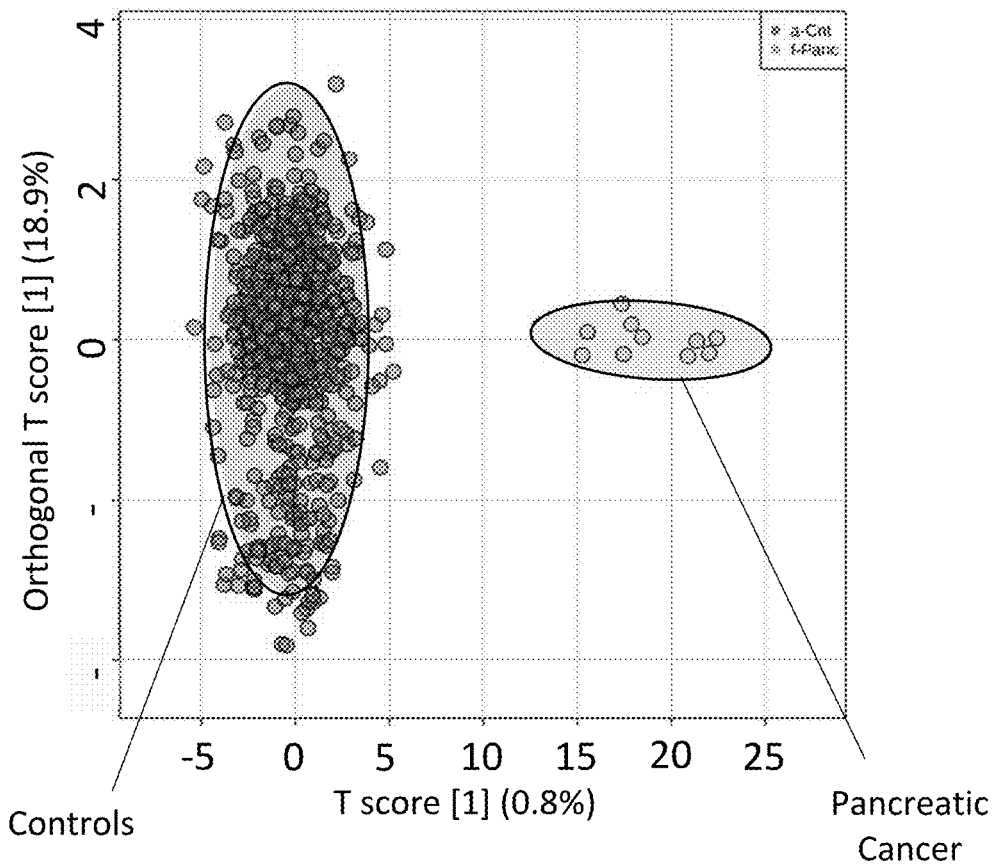
FIG. 21 provides an Ortho-PLSDA Score's plot for pancreatic cancer patients compared to healthy participants and other malignant and non-malignant conditions.

This can be seen, for example, in FIGS. 20A and B, showing that the signatures developed for assessing pancreatic cancer (i.e., one embodiment of the present invention) have a sensitivity of 100%, a specificity of 97.93%, and a negative predictive value of 100%. In particular, FIG. 20A shows a multivariate ROC curve analysis for pancreatic cancer patients (n-10) compared to healthy participants as well as other malignant and non-malignant conditions (n=709). FIG. 20B depicts the performance of the identified metabolites and ratios for pancreatic cancer patients. The 100% negative predictive value makes the present test highly indicative as a powerful screening tool.

FIG. 21 shows an Ortho-PLSDA Score's plot of pancreatic cancer patients (n=10) compared to healthy participants as well as other malignant and non-malignant conditions (n=709). By processing (e.g., isolating, quantifying, normalizing, etc.) each sample (e.g., blood sample), and then plotting the initial results (e.g., using an Ortho-PLSDA Score's plot) based on at least one pancreatic cancer signature (as identified by the inventors), each patient clearly falls within (a) the control group or (b) the pancreatic cancer group.

Moreover, portions of the signature provide details on each patient's prognosis. This can be seen, for example, in FIGS. 22A and B, where various equations (identified at the top of each chart) provide survival rate (prognosis) information for each patient. For example, FIG. 22A distinguishes short survival terms (e.g., 6 months) and longer survival terms (e.g., 15 months). FIG. 22B also distinguishes between short and long survival terms, but further validates that these findings were able to prove that the metabolic equation is fully functional in survival prediction even in malignancies of different origins, such as Multiple Myeloma (M.M.), Leukemias, Lymphomas and Myelodisplasias (where ISS 1, 2, and 3=Int'l Scaling System, Hem=Hematological Malignancies, and Panc=Pancreas Cancer). Thus, not only have the inventors identified signatures that can be used to diagnosis pancreatic cancer, but also to prognose pancreatic cancer.

Figure 22A:
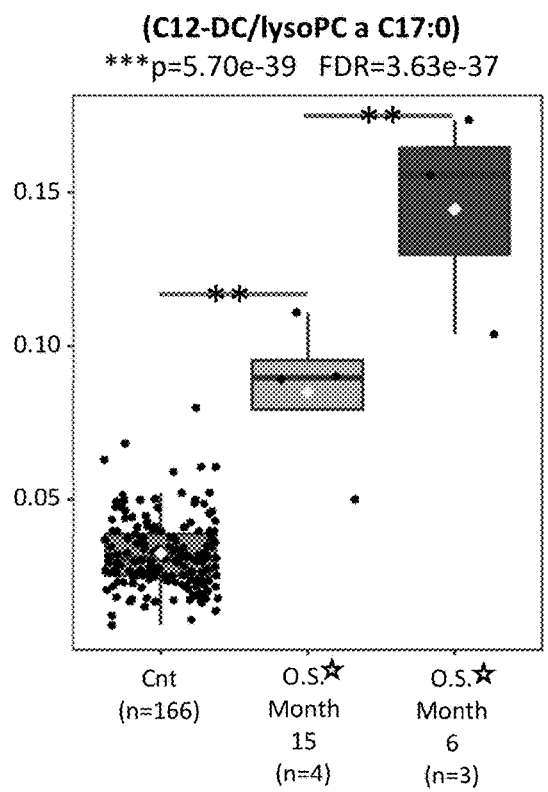
FIGS. 22A and B illustrate certain ratios that are useful in determining a survival rate (prognosis) for pancreatic cancer patients.
Figure 22B:
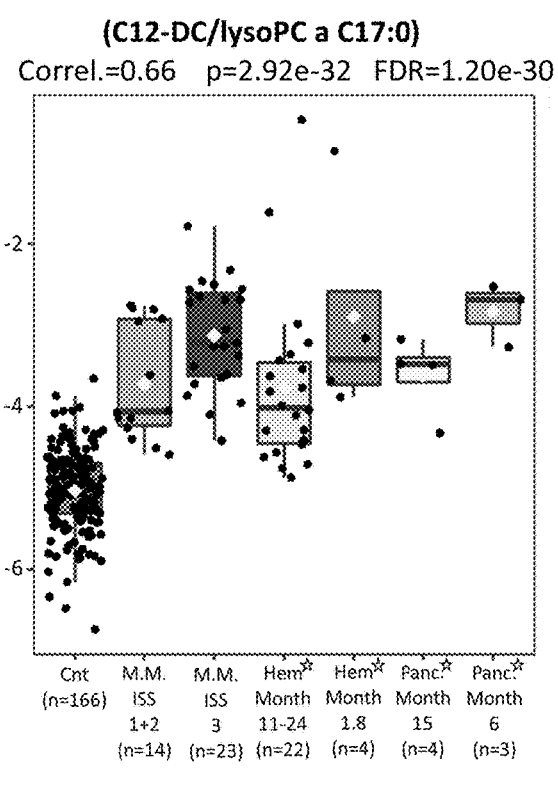

It should be appreciated that while the charts provided in FIGS. 21 and 22A-B illustrate (a) diagnosis for pancreatic cancer and (b) survival rates, the present invention is not so limited, and the pancreatic signatures (or portions thereof) can be used to provide other assessments for pancreatic cancer, including screening for, diagnosing, prognosing, treating the same as discussed in greater detail in the results section below.

A preferred signature (or portions thereof) for assessing pancreatic cancer is provided in FIG. 23, including a core pancreatic cancer equation, metabolite enhancers, and core equations with enhancers. As can be seen in FIG. 23, two core pancreatic cancer equations are (1) (C3:1/C12-DC), or a ratio of Propenoylcarnitine to Dodecanedioylcarnitine, and (2) (C6:1/C12-DC), or a ratio of Hexenoylcarnitine to Dodecanedioylcarnitine. See FIG. 3. The inventors have discovered that this ratio of individual metabolites, after quantification, normalization, etc., are critical in assessing a patient for pancreatic cancer. Other key portions include (C:12-DC/lysoPC a C17:0) and (C12-DC/lysoPC a C17:0), which can be used to not only diagnose, but prognose for pancreatic cancer.

Acute Graft Versus Host Disease (AGVHD) and Risk of Allogeneic Hematopoietic Stem Cell Transplantation (AHSCT) Signature Allogeneic hematopoietic stem cell transplantation (AHSCT) exemplifies the usage of an effective therapeutic strategy for a variety of hematological malignancies so that the flawlessness of the technique has nowadays lengthened its practice. Nevertheless, the technique is not free of any problem.

Indeed immunological-arbitrated difficulties, such as acute (AGVHD) and chronic graft-versus-host disease (CGVHD), usually observed in more than 50% of patients submitted to AHSCT remain a very important limiting factor in survival.

As a result, the indication for AHSCT should be more individualized and based on the expected long-term disease-free survival with conventional chemotherapy versus the risk of relapse and the risk of treatment related mortality/morbidity after transplantation.

Some strategies based on pre-transplantation prognostic factors are associated with long-term survival nevertheless; none of the available clinical and/or biochemical tools are capable to accurately predict the occurrence of AGVHD.

In view of the above-mentioned problems existing in the art, the object underlying the present invention is the provision of new biomarkers for assessing, prior to starting the allogeneic hematopoietic stem cell transplantation (AHSCT) procedures, the patients at increased risk to develop AGVHD.

Optimally, the marker should be easily detectable in a biological sample such as in blood and its level should be consistently related to the stage of hematological cancer. Moreover, it is an object of the present invention to provide for a method for assessing hematological cancer in a biological sample, which allows for fast, convenient and high throughput performance.

In order to solve the objects underlying the present invention the inventors based their investigations on metabolomics as it could give insight in the biochemical changes occurring in the course of hematological cancer development and offer several novel and potentially better biomarkers.

The inventors found that a more comprehensive picture of all metabolomics pathways and mechanisms involved in hematological malignancies is given when using a panel of metabolites that are altered in parallel of cancer behavior.

Therefore, in one embodiment of the present invention, new biomarkers (i.e. a new biomarker set) suitable for assessing, at baseline, the risk to develop AGVHD after allogeneic hematopoietic stem cell transplantation (AHSCT) transplant are provided.

Moreover, the present invention also provides for a method for assessing hematological cancer in a mammalian subject on the basis of the biomarkers and biomarker sets as described herein.

It has surprisingly been found in the present invention that the biomarkers and biomarker sets as described herein are particularly useful for fast, easy and high throughput screening of a large number of subjects, such as human patients, and for diagnosis of hematological cancer from blood samples of these subjects with improved accuracy of results.

Although accuracy and reliability of screening and/or diagnosis, as determined by the parameters of one or more of specificity, sensitivity, PPV and NPV, by using the above-specified biomarker combination is already greatly improved compared with the prior art techniques, such as ultrasound, the accuracy and reliability can be further improved by using one or more, preferably two or more, further preferably three or more additional metabolites.

Hence, in a preferred embodiment the biomarker set further comprises one or more additional amino acid, such as those included in FIG. 2. The additional amino acids are preferably selected from glucogenic/ketogenic amino acids such as glycine, cysteine, alanine, arginine, proline, aspartate, asparagine, methionine, isoleucine, leucine, lysine, threonine phenylalanine, tyrosine and tryptophan, most preferably asparagine and aspartate.

Moreover, the lipid is preferably selected from sphingolipids and glycerolipids, such as glycerophospholipids, e.g. one or more of the lipids included in FIGS. 4-6.

Further preferably, the lipid is derived from arachidonic acid, preferably arachidonic acid derived lipids containing 36 or more carbon atoms, and most preferably is selected from arachidonic polyunsaturated phosphatidylcholine acyl-alkyl or acyl-acyl, arachidonic mono-unsaturated phosphatidylcholine acyl-alkyl or acyl-acyl and arachidonic saturated phosphatidylcholine acyl-alkyl or acyl-acyl.

In a further preferred embodiment, the combination of metabolites further comprises one or more of lipids described in FIGS. 4-6 and one or more acylcarnitines as well as carnitine (C0) described in FIG. 3.

As the method of this embodiment can be performed from blood samples, the method greatly increases the subject's compliance compared to prior art screening techniques, such as ultrasound. In particular, the method greatly increases reliability and sensitivity of the screening results, in particular reduces the number of false positive and false negative results, and is less time consuming, and thus can be performed with a high number of patients.

Determining and Providing Results

The invention may involve a patient visiting a doctor, clinician, technician, nurse, etc., where blood or a different sample is collected. The sample would then be provided to a laboratory for analysis, as discussed above (e.g., mass spectrometry, log-transformation, comparisons, etc.). In another embodiment, a kit can be used to obtain the sample, where the kit is made available to the patient via a medical facility, a drug store, the Internet, etc. In this embodiment, the kit may include one or more wells and one or more inserts impregnated with at least one internal standard. The kit can be used to gather the sample from a patient, where the sample is then provided to a laboratory for analysis.

For example, as shown in FIG. 1, peripheral blood may collected into EDTA-anticoagulant tubes. Plasma is isolated by centrifugation. Plasma samples may then be submitted to a p180 AbsoluteIDQ kit for extraction and processing. In one embodiment, prepared samples will then undergo liquid chromatography (LC) followed by Flow Injection Analysis (FIA) by tandem Mass Spectrometry (MS/MS) (i.e., metabolite extraction). The extracted data is then processed using computer software. For example, the data acquired may then be normalized (e.g., via log-transformation) and stored in a database that includes at least (i) patient identification, (ii) metabolite name, and (iii) quantification. If this data is on known individuals (individuals with known conditions), then it can be analyzed to determine signatures that can be used to assess a particular disease. If, however, the data is on a patient whose condition is unknown, then it can be compared to known signatures (e.g., stored in memory) to screen for, diagnose, prognose, and treat the patient.

It should be appreciated that the present invention is not limited to normalizing a quantified metabolite. In other words, other processes discussed herein and/or generally known to those skilled in the art may be performed either before or after normalization. It should also be appreciated that while certain processes can be performed manually, most (if not all) should preferably be performed using software, where initial results (data post mass spectrometry, post normalization), are stored in memory, presented on a display (e.g., computer monitor, etc.) and/or printed. The initial results can then be compared to known "signatures" for different diseases, where similarities and differences are used to screen for, diagnose, prognose, treat, etc. a particular disease. It should be appreciated that the sample may be assessed for a particular disease, or for multiple diseases, depending on the patient's sex, age, etc. Thus, the software could be used to assess a particular disease or assess at least one disease from a plurality of diseases.

It should further be appreciated that the "comparing" step can be performed by (i) software, (ii) a human, or (iii) both. For example, with respect to the prior, a computer program could be used to compare sample results to known signatures and to use differences and/or similarities thereof to assess at least one disease, and provide diagnosis, prognosis, and/or treatment for the same. Alternatively, in the second embodiment, a technician could be used to compares sample results to known signatures (or aspects thereof) and make a diagnosis, prognosis, and/or treatment decision based on perceived similarities and/or differences. Finally, with respect to the latter, a computer program could be used to plot (e.g., on a computer display) sample results alongside known signatures (e.g., signatures of healthy patients, signatures of unhealthy patients, life expectancies, etc.). A technician could then view the same and make at least one diagnosis, prognosis, treatment recommendation, etc. based on similarities and/or differences in the plotted information.

Bottom line, it is the differences and/or similarities between known signatures that allows a disease to be assessed, whether that assessment is automated (e.g., performed by a computer), performed manually (e.g., done by a human), or a combination of the two.

Results (e.g., assessments) are then provided to the patient directly (e.g., via mail, an electronic communication, etc.) or via the patient's doctor, and can include screening information, diagnosis information, prognosis information, and treatment information.

In particular, the invention can be used to distinguish a sample that is cancerous from one that is normal. If it is cancerous, then the invention can further be used to distinguish, breast from ovary, ovary from lung, lung from colon, etc. Once the cancer is identified (e.g., ovarian, breast, etc.), the invention can be used to define the cancer, by degree, the relative malignancy of the cancer. This can be done using terminology (e.g., non-invasive (e.g., in situ), invasive, metastatic, and lethal), at least one scale (e.g., 1-10, 1-100, A-F, etc.), where one end of the scale is low grade (e.g., non-invasive) and the other end is high grade (lethal), or other visual forms (e.g., color coded, 2D or 3D model, etc.).

The invention can also be used to provide a prognosis. For example, in ovarian cancer, once the ovarian signature is identified, the invention can be used to provide gradations within the signature (or signatures), subcategorizing the patient into one that is likely to survive (e.g., greater than 3 years, 5 years, 10 years, etc.), likely to relapse (e.g., within 3 years, 5 years, 10 years, etc.), or likely to die (e.g., within 3 years, 5 years, 10 years, etc.). Again, prognosis could be provided using terminology (e.g., low risk, medium risk, high risk, etc.), at least one scale, or other visual forms.

Not only can the present invention be used to determine life expectancy and remission rate, it can also be used to determine treatment, or viability of treatment (another form of prognosis). This could be a likelihood to respond to therapy (e.g., hormonal, radiation, chemotherapy, etc.), which again could be provided using terminology, at least one scale, or other visual forms.

Thus, by way of example, the present invention may be used to determine (i) a high likelihood that a patient harbors a cancer (diagnosis), (ii) a high likelihood that the cancer is ovarian (diagnosis), (iii) likely drug resistant (prognosis), (iv) high risk of relapse (prognosis), and (v) high risk of death within 3-5 years (prognosis). Clearly this is exemplary, and other diseases (e.g., breast, colon, ovarian, etc.), sub-categorizations (e.g., indolent, aggressive, very aggressive, etc.), prognosis (e.g., reoccurrence within 3 years, 5 years, 10 years, etc.), and treatments (e.g., resistant to hormonal therapy, chemotherapy, radiation therapy, etc.) can be identified (predicted) using the present invention.

The invention can also be used to screen for diseases. Medical screening is the systematic application of a test or inquiry to identify individuals at sufficient risk of a specific disorder to benefit from further investigation or direct preventative action (these individuals not having sought medical attention on account of symptoms of that disorder). The present invention uses metabolic signatures to screen for diseases in populations who are considered at risk. For ovarian cancer, this may be woman in their 40s or 50s with a family history, or other risk factors.

It should be appreciated that while several examples have been provided as to what the present invention can discern from a blood sample (or the like), the present invention is not so limited, and other types of diagnosis and prognosis, including treatments, are within the spirit and scope of the present invention. For example, breast cancer may be identified as ductal, tubular, medullary, mucinous, papillary, cribriform, lobular, etc. It may also be identified by its prognosis (e.g., triple negative, etc.). Those skilled in the art will understand that similar classifications can be provided for other cancers, where such classification are generally known to those skilled in the art. All such classifications, for both diagnosis and prognosis, are within the spirit and scope of the present invention.

As shown in FIG. 1, once a sample has been received and processed (e.g., processed using techniques like the one used to identify the signatures in the first place, such as mass spectrometry (to quantify metabolites), log-transformation (or other mathematical manipulation to normalize the data), etc.), the initial results (e.g., metabolites and/or sets thereof) can then be compared to signatures (or portions thereof) that have been identified (by the inventors) as useful in assessing at least one disease. The signatures may be stored in memory, and the initial data (i.e., processed sample) may be compared to at least one signature either manually (e.g., by viewing the sample, or initial results thereof, against known signatures), automatically (e.g., using a computer program to discern differences and/or similarities between the sample, or initial results thereof, and known signatures), or both (e.g., a program determines at least one diagnosis/prognosis and a technician reviews the data to validate the same). Based on the results (i.e., comparison results), at least one diagnosis and/or prognosis, which may or may not include treatment, is identified and provided to the patient.

CONCLUSION

Having thus described several embodiments of a system and method for using new biomarkers for assessing different diseases, it should be apparent to those skilled in the art that certain advantages of the system and method have been achieved. It should also be appreciated that various modifications, adaptations, and alternative embodiments thereof may be made within the scope and spirit of the present invention. The invention is solely defined by the following claims.

What is claimed is:

1. A method for assessing a human patient for ovarian cancer, comprising:

using a technology selected from chromatography, spectroscopy, and spectrometry to quantify a plurality of metabolites included in a blood sample obtained from said human patient, including at least Tiglylcarnitine and Glutaconylcarnitine;

normalizing data values obtained in the quantification of at least said Tiglylcarnitine and said Glutaconylcarnitine, as quantified using said technology;

comparing at least a result of an equation comprising at least a first ratio of said Tiglylcarnitine to said Glutaconylcarnitine, as quantified and normalized, to at least one predetermined value to both diagnose said human patient for said ovarian cancer and determine a prognosis for said human patient;

wherein said diagnosis includes whether said human patient has ovarian cancer and said prognosis includes a response to treatment for ovarian cancer, said response to treatment comprising whether chemotherapy will likely result in pathological complete remission (pCR), and therefore whether said chemotherapy should be used to treat said human patient; and administering chemotherapy to said human patient when said prognosis, including said response to treatment for ovarian cancer, indicates that doing so to said human patient will result in pCR.

2. The method of claim 1, further comprising steps of quantifying Dodecanedioylcarnitine and then normalizing said quantified Dodecanedioylcarnitine, wherein said equation further comprises at least a second ratio of said Dodecanedioylcarnitine, as quantified and normalized, to said first ratio.

3. The method of claim 1, further comprising steps of quantifying and normalizing Octadecenoylcarnitine and Aspartate, where said equation further comprises at least a second ratio of said Octadecenoylcarnitine to said Aspartate, as quantified and normalized.

4. The method of claim 3, wherein said equation further comprises at least a third ratio comprising at least said second ratio to said first ratio.

5. The method of claim 1, further comprising steps of quantifying and normalizing Ornithine, Arginine, and Tryptophan, and comparing at least a second result of a second equation comprising said Ornithine, said Arginine, and said Tryptophan, as quantified and normalized to at least one other predetermined value to determine said prognosis for said human patient.

6. The method of claim 1, further comprising steps of quantifying and normalizing Ornithine, Aspartate, Octadecenoylcarnitine, and comparing at least a second result of a second equation comprising said Ornithine, said Aspartate, and said Octadecenoylcarnitine, as quantified and normalized, to at least one other predetermined value to determine said prognosis for said human patient.

7. The method of claim 1, wherein said step of normalizing data values obtained in the quantification of at least said Tiglylcarnitine and said Glutaconylcarnitine further comprises using at least a log-transformation to normalize said data values obtained in the quantification of at least said Tiglylcarnitine and said Glutaconylcarnitine.

8. The method of claim 1, wherein said prognosis further comprises a survival rate of said human patient from said ovarian cancer.

9. The method of claim 1, wherein said prognosis further comprises a degree of said ovarian cancer, said degree being one of non-invasive, invasive, metastatic, and lethal.

10. The method of claim 1, wherein said prognosis further comprises a relapse rate of said ovarian cancer.

* * * * *